United States Patent [19]

Misslitz et al.

[11] Patent Number: 5,739,085
[45] Date of Patent: Apr. 14, 1998

[54] O-(OXIMINO)ETHYLCYCLOHEXENONE OXIME ETHERS AND THEIR USE AS HERBICIDES

[75] Inventors: Ulf Misslitz, Neustadt; Albrecht Harreus, Ludwigshafen; Hartmann König, Heidelberg; Helmut Walter, Obrigheim; Karl-Otto Westphalen, Speyer; Matthias Gerber, Limburgerhof, all of Germany

[73] Assignee: BASF Aktiengesellschaft, Ludwigshafen, Germany

[21] Appl. No.: 435,450

[22] Filed: May 5, 1995

[51] Int. Cl.[6] .................. A01N 33/24; A01N 41/06; A01N 43/16; A01N 43/18
[52] U.S. Cl. .................. 504/344; 504/271; 504/288; 504/292; 504/333; 548/247; 548/249; 549/13; 549/426; 564/98; 564/99; 564/256
[58] Field of Search .................. 549/13, 426; 504/288, 504/271, 292, 333, 344; 548/247, 249; 564/256, 98, 99

[56] References Cited

U.S. PATENT DOCUMENTS

| | | | |
|---|---|---|---|
| 3,502,452 | 3/1970 | Patinkin | 44/69 |
| 4,249,937 | 2/1981 | Iwataki et al. | 71/97 |
| 4,440,566 | 4/1984 | Luo et al. | 71/98 |
| 4,880,456 | 11/1989 | Kolassa et al. | 71/88 |
| 5,022,914 | 6/1991 | Kast et al. | 71/88 |
| 5,100,532 | 3/1992 | Roling et al. | 208/48 AA |
| 5,190,573 | 3/1993 | Misslitz et al. | 504/292 |
| 5,228,896 | 7/1993 | Misslitz et al. | 504/288 |
| 5,250,505 | 10/1993 | Kast et al. | 504/292 |
| 5,364,833 | 11/1994 | Kast et al. | 504/289 |
| 5,374,609 | 12/1994 | Kast et al. | 504/344 |

FOREIGN PATENT DOCUMENTS

| | | |
|---|---|---|
| 080 301 | 6/1983 | European Pat. Off. . |
| 125 094 | 11/1984 | European Pat. Off. . |
| 478 001 | 4/1992 | European Pat. Off. . |
| 92/08696 | 5/1992 | WIPO . |
| 93/10081 | 5/1993 | WIPO . |
| 93/16033 | 8/1993 | WIPO . |
| 9316033 | 8/1993 | WIPO . |

OTHER PUBLICATIONS

*Chem. Abst.*, vol. 107, No. 17, 1987, Abst. No. 154026c.
Chem Abst. 105:114646 Wroblowsky et al. EP172551 26 Feb. 1986.

Derwent 93–265436/34 Gerber et al. WO 9316061 Aug. 1993.

Derwent 93–265438/34 Berger et al. WO 93 16062 Aug. 1993.

Kishimoto et al. Chem Abst. 114:6034, 1990.

*Primary Examiner*—Peter O'Sullivan
*Attorney, Agent, or Firm*—Keil & Weinkauf

[57] ABSTRACT

O-(Oximino)ethylcyclohexenone oxime ethers I

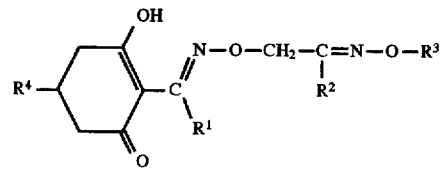

($R^1$ and $R^2 = C_1$–$C_6$-alkyl;

$R^3$ = unsubstituted or substituted phenyl, $C_1$–$C_4$-alkyl, $C_3$–$C_4$-alkenyl or $C_3$–$C_4$-alkynyl, which in each case can be substituted by halogen, $C_1$–$C_3$-alkyl, unsubstituted or substituted phenyl or unsubstituted or substituted phenoxy;

$R^4 = C_1$–$C_4$-alkoxy-$C_1$–$C_6$-alkyl or $C_1$–$C_4$-alkylthio-$C_1$–$C_6$-alkyl, unsubstituted or substituted phenylthio-$C_1$–$C_6$-alkyl, N-($C_1$–$C_4$-alkylsulfonyl)-N-($C_1$–$C_4$-alkyl)aminomethyl, unsubstituted or substituted $C_3$–$C_7$-cycloalkyl or $C_5$–$C_7$-cycloalkenyl, 5-membered saturated heterocyclyl having one or two oxygen and/or sulfur atoms, which can carry one to three substituents, saturated or unsaturated 6-/7-membered heterocyclyl having 1 or 2 non-adjacent oxygen and/or sulfur atoms, which can carry 1 to 3 substituents, 5-membered heteroaryl, containing 1 to 2 nitrogen atoms and an oxygen or sulfur atom, where the heteroaromatic can carry 1 to 3 substituents, phenyl or pyridyl, which can carry 1 to 3 of the following substituents: halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and —$NR^aR^b$;

$R^a$ = H, $C_1$–$C_4$-alkyl, $C_3$–$C_6$-alkenyl or $C_3$–$C_6$-alkynyl;

$R^b$ = H, $C_1$–$C_4$-alkyl, $C_3$–$C_6$-alkenyl, $C_3$–$C_6$-alkynyl, $C_1$–$C_6$-acyl or unsubstituted or substituted benzoyl)

and their agriculturally utilizable salts and esters are described.

6 Claims, No Drawings

O-(OXIMINO)ETHYLCYCLOHEXENONE OXIME ETHERS AND THEIR USE AS HERBICIDES

The present invention relates to novel O-(oximino) ethylcyclohexenone oxime ethers of the formula I

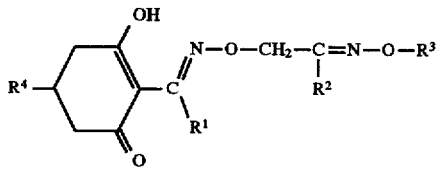

where the substituents have the following meanings:

$R^1$ is a $C_1$–$C_6$-alkyl group;

$R^2$ is a $C_1$–$C_6$-alkyl group;

$R^3$ is the phenyl group, which can be unsubstituted or can carry one to three substituents selected from the group consisting of nitro, cyano, halogen, $C_1$–$C_4$-alkyl and $C_1$–$C_4$-haloalkyl;

a $C_1$–$C_4$-alkyl, $C_3$–$C_4$-alkenyl or $C_3$–$C_4$-alkynyl group, these groups if desired being able to carry one of the following substituents:

halogen, $C_1$–$C_3$-alkyl, phenyl which, if desired, in turn can carry one to three radicals selected from the group consisting of nitro, cyano, halogen, $C_1$–$C_4$-alkyl, $C_1$–$C_4$-haloalkyl, phenyl and phenoxy, or phenoxy which, if desired, in turn can carry one to three radicals selected from the group consisting of nitro, cyano, halogen, $C_1$–$C_4$-alkyl and $C_1$–$C_4$-haloalkyl;

$R^4$ is a $C_1$–$C_4$-alkoxy-$C_1$–$C_6$-alkyl or $C_1$–$C_4$-alkylthio-$C_1$–$C_6$-alkyl group;

a phenylthio-$C_1$–$C_6$-alkyl group, the phenyl ring if desired being able to carry one to three substituents selected from the group consisting of halogen and $C_1$–$C_4$-haloalkyl;

an N-($C_1$–$C_4$-alkylsulfonyl)-N-($C_1$–$C_4$-alkyl) aminomethyl group;

a $C_3$–$C_7$-cycloalkyl or $C_5$–$C_7$-cycloalkenyl group, where these groups can be unsubstituted or in each case can carry one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl;

a 5-membered saturated heterocycle which contains one or two oxygen and/or sulfur atoms as heteroatoms and which can be unsubstituted or can carry one to three substituents selected from the group consisting of $C_1$–$C_4$-alkyl, $C_1$–$C_4$-alkoxy, $C_1$–$C_4$-alkylthio and $C_1$–$C_4$-haloalkyl;

a 6- or 7-membered heterocycle having one or two non-adjacent oxygen and/or sulfur atoms as heteroatoms, which can be saturated or mono- or diunsaturated, where the heterocycle can be unsubstituted or can carry one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl;

a 5-membered heteroaromatic containing one or two nitrogen atoms and an oxygen or sulfur atom, where the heteroaromatic can be unsubstituted or can carry one to three substituents selected from the group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy and $C_1$–$C_4$-alkoxy-$C_1$–$C_4$-alkyl;

the phenyl or pyridyl group, where these groups can be unsubstituted or in each case can carry one to three substituents selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and —$NR^aR^b$, where $R^a$ is hydrogen, $C_1$–$C_4$-alkyl, $C_3$–$C_6$-alkenyl or $C_3$–$C_6$-alkynyl and $R^b$ is hydrogen, $C_1$–$C_4$-alkyl, $C_3$–$C_6$-alkenyl, $C_3$–$C_6$-alkynyl, $C_1$–$C_6$-acyl or benzoyl which if, desired, in turn can carry one to three radicals selected from the group consisting of nitro, cyano, halogen, $C_1$–$C_4$-alkyl, $C_1$–$C_4$-alkoxy, $C_1$–$C_4$-alkylthio and $C_1$–$C_4$-haloalkyl, and the agriculturally utilizable salts of I and the esters of I with $C_1$–$C_{10}$-carboxylic acids or inorganic acids.

The invention additionally relates to the use of these compounds as herbicides, to herbicidal compositions which contain these compounds as active substances, to processes for the production of these herbicidal compositions and to processes for controlling undesired plant growth using the compounds I.

The invention in addition relates to novel O-(oximino) ethylhydroxylamines of the formula III

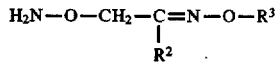

where $R^2$ is a $C_1$–$C_6$-alkyl group and $R^3$ is the phenyl group, which can be unsubstituted or can carry one to three substituents selected from the group consisting of nitro, cyano, halogen, $C_1$–$C_4$-alkyl and $C_1$–$C_4$-haloalkyl or a $C_1$–$C_4$-alkyl, $C_3$–$C_4$-alkenyl or $C_3$–$C_4$-alkynyl group, where these groups if desired can carry one of the following substituents: halogen, $C_1$–$C_3$-alkyl, phenyl which can be unsubstituted or in turn can carry one to three radicals selected from the group consisting of nitro, cyano, halogen, $C_1$–$C_4$-alkyl, $C_1$–$C_4$-haloalkyl, phenyl and phenoxy, or phenoxy which if desired in turn can carry one to three radicals selected from the group consisting of nitro, cyano, halogen, $C_1$–$C_4$-alkyl and $C_1$–$C_4$-haloalkyl, and the ammonium salts of the compounds III with inorganic acids.

Herbicidally effective cyclohexane diones of the formula I'

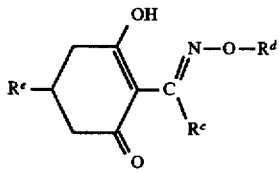

have already been disclosed in the literature, $R^c$, $R^d$ and $R^e$ having, inter alia, the following meanings:

U.S. Pat. No. 4,249,937 ($R^c$=lower alkyl; $R^d$=alkyl, alkenyl; $R^e$=2-(4-chlorophenylthio) ethylene);

WO 92/08696 ($R^c$=$C_1$–$C_6$-alkyl; $R^d$=benzyl; $R^e$=N-(methylsulfonyl)-N-methyl-aminomethyl);

WO 93/10081 ($R^c$=$C_1$–$C_6$-alkyl; $R^d$=substituted 3-phenylpropenylene radical; $R^e$=$C_1$–$C_6$-alkyl);

U.S. Pat. No. 4,440,566 ($R^c$=$C_1$–$C_6$-alkyl; $R^d$=benzyl; $R^e$=2-ethylthiopropyl);

EP-A 238 021 and EP-A 125 094 ($R^c$=$C_1$–$C_4$- or $C_1$–$C_6$-alkyl; $R^d$=benzyl, but-2-enyl; $R^e$=substituted 5-membered heteroaryl radical);

EP-A 80 301 ($R^c$=$C_1$-$C_6$-alkyl; $R^d$=benzyl, but-2-enyl; $R^e$=substituted phenyl);

DE-A 38 38 309 ($R^c$=$C_1$-$C_6$-alkyl; $R^d$=substituted 4-phenylbutylene or 4-phenylbutenylene radical; $R^e$=substituted 5- to 7-membered heterocycle);

EP-A 456 112 ($R^c$=$C_1$-$C_6$-alkyl; $R^d$=substituted 3-phenoxypropylene or 2-phenoxyethylene radical; $R^e$=substituted 5- to 7-membered heterocycle);

WO 93/16,063 ($R^c$=$C_1$-$C_6$-alkyl; $R^d$=substituted (benzylideneiminooxy)alkylene radical; $R^e$=substituted 5-7-membered heterocycle);

Since the herbicidal properties of the known compounds, in particular with respect to their selectivity against grass weeds in graminaceous crop plants, are not always completely satisfactory, it is an object of the present invention to provide novel cyclohexenone oxime ethers with which grass weeds in graminaceous crops such as rice and maize can be specifically controlled better than previously.

We have found that this object can be achieved by the O-(oximino)ethylcyclohexenone oxime ethers I defined at the outset, their use as herbicides, herbicidal compositions which contain the compounds I, a process for the production of these compositions and a process for controlling undesired plant growth using the compounds I.

The O-(oximino)ethylcyclohexenone oxime ethers I are obtainable in various ways, ie. preferably in a manner known per se from already disclosed cyclohexenones of the formula II (cf. eg. DE-A 38 38 309, EP-A 456 112, U.S. Pat. No. 4,249,937 and WO 92/08696) and O-(oximino) ethylhydroxylamines of the formula III:

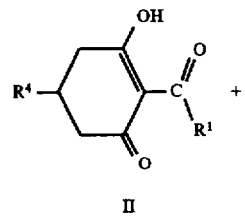

II

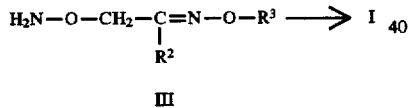

III

Preferably a salt of the hydroxylamine III is used, in particular its hydrochloride, and the reaction is carried out in the heterogeneous phase in an inert solvent, for example in dimethyl sulfoxide, in an alcohol such as methanol, ethanol or isopropanol, in an aromatic hydrocarbon such as benzene or toluene, in a chlorinated hydrocarbon such as chloroform or 1,2-dichloroethane, in an aliphatic hydrocarbon such as hexane or cyclohexane, in an ester such as ethyl acetate or in an ether such as diethyl ether, dioxane or tetrahydrofuran.

The reaction is carried out in the presence of a base, normally an amount of base of from about 0.5 to 2 mol equivalents, based on the ammonium compound, being sufficient.

Suitable bases are eg. carbonates, hydrogencarbonates, acetates, alkoxides or oxides of alkali metals or alkaline earth metals, in particular sodium hydroxide, potassium hydroxide, magnesium oxide or calcium oxide. In addition, organic bases such as pyridine and tert-amines such as triethylamine are suitable.

The reaction is preferably carried out in methanol using sodium hydrogencarbonate as a base.

One variant of the process consists in carrying out the reaction with the free hydroxylamine base III without base, eg. in the form of an aqueous solution; depending on the solvent used for the compound II a one- or two-phase reaction mixture is obtained.

Suitable solvents for this variant are, for example, alcohols such as methanol, ethanol, isopropanol and cyclohexanol, aliphatic and aromatic hydrocarbons, which may be chlorinated, such as hexane, cyclohexane, methylene chloride, toluene and dichloroethane, esters such as ethyl acetate, nitriles such as acetonitrile and cyclic ethers such as dioxane and tetrahydrofuran.

Expediently, the cyclohexenone II and the O-(oximino) ethylhydroxylamine III or its salt is employed in an approximately stoichiometric ratio, but in some cases an excess of one component or the other, up to about 10 mol%, may be advantageous.

The reaction temperature is in general from 0° C. to the boiling point of the reaction mixture, preferably from 20° to 80° C.

The reaction is complete after a few hours. The product can be isolated in a customary manner, eg. by concentration of the mixture, partition of the residue in methylene chloride/water and removal of the solvent by distillation under reduced pressure.

No particular conditions with respect to the pressure are to be observed; in general the reaction is therefore carried out at normal pressure or under the autogenous pressure of the particular diluent.

The cyclohexenone oxime ethers I according to the invention can be present in the form of their agriculturally utilizable salts or as enol esters, where the nature of the salt or ester in general does not matter. As a rule, those bases are suitable for salt formation and those acids are suitable for esterification which do not adversely affect the herbicidal action of I.

Alkali metal salts of the compounds I can be obtained by treating the 3-hydroxycyclohexenone compounds with sodium or potassium hydroxide or alkoxide in aqueous solution or in an organic solvent such as methanol, ethanol, acetone or toluene.

Other metal salts such as manganese, copper, zinc, iron, calcium, magnesium and barium salts can be prepared from the sodium salts in a customary manner, as well as ammonium, phosphonium, sulfonium and sulfoxonium salts by means of ammonium, phosphonium, sulfonium or sulfoxonium hydroxides.

The esters of the compounds I are likewise obtainable in a customary manner (cf. eg. Organikum, VEB Deutscher Verlag der Wissenschaften, 17th edition, Berlin 1988, pp. 405–408).

The novel O-(oximino)ethylhydroxylamines of the formula III can be prepared from known precursors via a series of process steps known per se. Preferably, an N-(2-oxo-1-alkoxy)phthalimide IV {cf. Pharmazie 25, 400 (1970)} is coupled in a manner known for ketones (for this see eg. Houben-Weyl, Methoden der organischen Chemie, [Methods of Organic Chemistry], Vol. E 14b, p. 369) with a hydroxylamine V (U.S. Pat. No. 4,249,937, WO 92/08696, WO 93/10081, U.S. Pat. No. 4,440,566, EP-A 238 021, EP-A 080 301, DE-A 38 38 309, EP-A 456 112, WO 93/16033, WO 93/1602) with elimination of water:

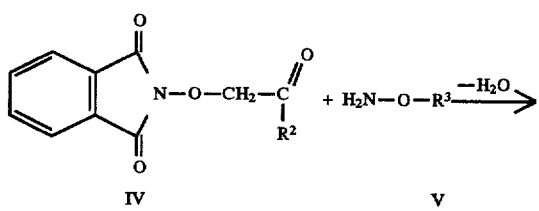

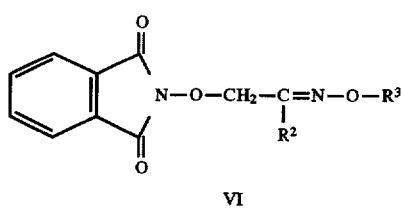

Depending on the substituents $R^2$ and $R^3$, the O-(oximino)ethylhydroxylamines III and the O-(oximino) ethylcyclohexenone oxime ethers I can be obtained during the preparation as an isomer mixture, both E/Z isomer mixtures and (R/S) enantiomer mixtures or diastereomer mixtures being possible. If desired, the isomer mixtures can be separated by the methods customary for this purpose, eg. by chromatography or by crystallization.

The O-(oximino)ethylcyclohexenone oxime ethers I can be written in several tautomeric forms, which are all covered by the invention:

The oxime ether derivatives VI can be isolated from the reaction mixtures obtained by this process by means of

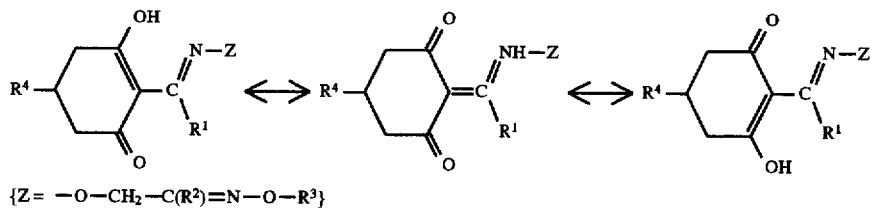

$\{Z = -O-CH_2-C(R^2)=N-O-R^3\}$ customary working-up methods, for example by extraction or by crystallization.

Before their conversion to the O-(oximino) ethylhydroxylamines III, the oxime ether derivatives VI can, if desired, be intermediately stored.

The conversion to the O-(oximino)ethylhydroxylamines III (having a free amino group) can likewise be carried out by processes known per se. To this end, reference may in particular be made to the details in DE-A 36 15 973 and in the publications cited therein. Preferably, the process as described in DE-A 36 15 973 is used, according to which the hydroxylamines III were liberated by means of ethanolamine. The liberation of the hydroxylamines III with the aid of other bases such as aqueous inorganic bases, with amines, hydrazines, hydroxylamines or by means of aqueous acids, however, is likewise possible:

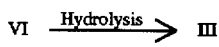

The O-(oximino)ethylhydroxylamines III can be isolated from the resulting reaction mixtures by means of customary working-up methods, for example by extraction or by crystallization. To increase the tendency for crystallization, it may often be beneficial to convert the hydroxylamines to their salts using inorganic acids or organic acids. To do this, dilute solutions of the acids are in general employed, approximately stoichiometric amounts of acid and hydroxylamine derivative being expedient.

Like the O-(oximino)ethylhydroxylamines III (having a free amino group), the hydroxylammonium salts obtained can be directly processed further to give the herbicides of the formula I or alternatively, if desired, stored.

The collective terms used in the definitions of the substituents halogen, $C_1-C_6$-alkyl group, $C_1-C_4$-alkyl, $C_1-C_3$-alkyl, $C_1-C_4$-alkoxy, $C_1-C_4$-alkylthio, $C_1-C_4$-alkylsulfonyl, $C_1-C_4$-haloalkyl, $C_3-C_7$-cycloalkyl group, $C_5-C_7$-cycloalkenyl group, $C_2-C_6$-alkenyl, $C_3-C_6$-alkenyl, $C_3-C_4$-alkenyl group, $C_2-C_6$-alkenyloxy, $C_3-C_6$-alkynyl, $C_3-C_4$-alkynyl group, $C_3-C_6$-alkynyloxy, N-($C_1-C_4$-alkylsulfonyl)-N-($C_1-C_4$-alkyl)aminomethyl group, $C_1-C_4$-alkoxy-$C_1-C_4$-alkyl, $C_1-C_4$-alkoxy-$C_1-C_6$-alkyl group, $C_1-C_4$-alkylthio-$C_1-C_6$-alkyl group, $C_1-C_6$-acyl are brief notations for a separate list of the individual group members. All the alkyl, alkoxy, alkylthio, alkylsulfonyl, haloalkyl, alkenyl, alkenyloxy, alkynyl, alkynyloxy and acyl moieties can be straight-chain or branched. The haloalkyl moieties can carry identical or different halogen atoms.

Specific meanings are, for example halogen: fluorine, chlorine, bromine, iodine;

$C_1-C_6$-alkyl group: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1methylpropyl, 1-ethyl-2-methylpropyl;

$C_1$–$C_4$-alkyl (group): methyl, ethyl, n-propyl, 1-methylethyl, n-butyl, 1-methylpropyl, 2-methylpropyl, 1,1-dimethylethyl;

$C_1$–$C_3$-alkyl: methyl, ethyl, n-propyl, 1-methylethyl;

$C_1$–$C_4$-alkoxy: methoxy, ethoxy, n-propoxy, 1-methylethoxy, n-butoxy, 1-methylpropoxy, 2-methylpropoxy, 1,1-dimethylethoxy;

$C_1$–$C_4$-alkylthio: methylthio, ethylthio, n-propylthio, 1-methylethylthio, n-butylthio, 1-methylpropylthio, 2-methylpropylthio, 1,1-dimethylethylthio;

$C_1$–$C_4$-haloalkyl: $C_1$–$C_4$-alkyl as mentioned above, which is partly or completely substituted by fluorine, chlorine and/or bromine, that is eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloropropyl, heptafluoropropyl; $C_2$–$C_6$-alkenyl: ethenyl and $C_3$–$C_6$-alkenyl such as 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl;

$C_3$–$C_4$-alkenyl group: 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl;

$C_2$–$C_6$-alkenyloxy: ethynyloxy and $C_3$–$C_6$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 4-methyl-4-pentenyloxy, 1,1-dimethyl-2-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-2-propenyloxy;

$C_3$–$C_6$-alkynyl: prop-1-yn-1-yl, Prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yt, 4-methyl-pent-1-yn-1-yl, 4-methyl-pent-2-yn-4-yl, 4-methyl-pent-2-yn-5-yl;

$C_3$–$C_4$-alkynyl group: prop-1-yn-1-yl, prop-2-yn-3-yl, n-but-1-yn-1-yl, n-but-1-yn-4-yl, n-but-2-yn-1-yl;

$C_3$–$C_6$-alkynyloxy: prop-1-yn-1-yloxy, prop-2-yn-3-yloxy, n-but-1-yn-1-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methyl-but-1-yn-1-yloxy, 3-methyl-but-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methyl-pent-1-yn-1-yloxy, 3-methyl-pent-1-yn-3-yloxy, 3-methyl-pent-1-yn-4-yloxy, 3-methyl-pent-1-yn-5-yloxy, 4-methyl-pent-1-yn-1-yloxy, 4-methyl-pent-2-yn-4-yloxy, 4-methyl-pent-2-yn-5-yloxy;

$C_3$–$C_7$-cycloalkyl group: cyclopropyl, cyclobutyl, cyclopentyl, cyclohexyl, cycloheptyl;

$C_5$–$C_7$-cycloalkenyl: eg. cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl.

With respect to the herbicidal activity of the O-(oximino) ethylcyclohexenone oxime ethers I, the following meanings of the substituents, namely per se or in combination, are particularly preferred:

$R^1$ ethyl and propyl;

$R^2$ methyl;

$R^3$ the phenyl group, unsubstituted or mono- to trisubstituted by nitro, cyano;

halogen, in particular fluorine, chlorine;

$C_1$–$C_4$-alkyl, in particular methyl;

$C_1$–$C_4$-haloalkyl, in particular trifluoromethyl;

a $C_1$–$C_4$-alkyl, $C_3$–$C_4$-alkenyl or $C_3$–$C_4$-alkynyl group, where these groups if desired can carry one of the following substituents:

halogen, in particular fluorine, chlorine;

$C_1$–$C_3$-alkyl, in particular methyl;

phenyl, which can be unsubstituted or can carry one to three substituents selected from the group consisting of nitro, cyano;
halogen, in particular fluorine, chlorine;
$C_1$–$C_4$-alkyl, in particular methyl;
$C_1$–$C_4$-haloalkyl, in particular trifluoromethyl;
phenyl, phenoxy;
phenoxy, which can be unsubstituted or can carry one to three substituents selected from the group consisting of
nitro, cyano;
halogen, in particular fluorine, chlorine;
$C_1$–$C_4$-alkyl, in particular methyl;
$C_1$–$C_4$-haloalkyl, in particular trifluoromethyl;

$R^4$ a $C_1$–$C_6$-alkyl group as mentioned above, which is substituted by $C_1$–$C_4$-alkoxy, in particular methoxy, ethoxy, 1-methylethoxy or 1,1-dimethylethoxy, or by $C_1$–$C_4$-alkylthio, in particular methylthio or ethylthio, namely preferably in the 1-, 2- or 3-position; 2-ethylthiopropyl is very particularly preferred;

a phenylthio-$C_1$–$C_6$-alkyl group, in particular the 2-(phenylthio)ethyl group, where the phenyl ring if desired can carry one to three halogen atoms, in particular fluorine and/or chlorine atoms, and/or $C_1$–$C_4$-haloalkyl radicals, in particular trifluoromethyls;

an N-($C_1$–$C_4$-alkylsulfonyl)-N-($C_1$–$C_4$-alkyl) aminomethyl group; in particular the N-methylsulfonyl-N-methylaminomethyl or N-ethylsulfonyl-N-methylaminomethyl group;

a $C_3$–$C_7$-cycloalkyl or $C_5$–$C_7$-cycloalkenyl group which if desired can carry one to three of the following radicals:
$C_1$–$C_4$-alkyl, $C_1$–$C_4$-alkoxy, $C_1$–$C_4$-alkylthio and/or $C_1$–$C_4$-haloalkyl; 1-methylthio-1-cyclopropyl is very particularly preferred;

a 5-membered saturated heterocycle such as tetrahydrofuranyl, tetrahydrothienyl, dioxolanyl, dithiolanyl and oxathiolanyl, in particular tetrahydrofuranyl, tetrahydrothienyl and dioxolanyl, where the heterocycle can be unsubstituted or can carry one to three radicals selected from the group consisting of $C_1$–$C_4$-alkyl, $C_1$–$C_4$-alkoxy, $C_1$–$C_4$-alkylthio and $C_1$–$C_4$-haloalkyl;

a 6- or 7-membered heterocycle which
a) can be saturated, eg. tetrahydropyranyl, tetrahydrothiopyranyl, oxepanyl, thiepanyl and dioxepan-5-yl,
b) can be mono- or diunsaturated, eg. dihydropyran-3-yl, dihydropyran-4-yl, dihydrothiopyran-3-yl and dihydrothiopyran-4-yl,
where the heterocycles can be unsubstituted or can carry one to three radicals selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl;
tetrahydropyran-3-yl, tetrahydropyran-4-yl and tetrahydrothiopyran-3-yl are very particularly preferred;

a 5-membered heteroaromatic such as pyrrolyl, pyrazolyl, imidazolyl, isoxazolyl, oxazolyl, isothiazolyl, thiazolyl, furanyl, thienyl, 1,2,4-oxadiazolyl, 1,2,4-thiadiazolyl, 1,3,4-oxadiazol-2-yl and 1,3,4-thiadiazol-2-yl, preferably isoxazolyl and furanyl, where the heteroaromatic can be unsubstituted or can carry one to three radicals selected from the group consisting of
$C_1$–$C_4$-alkyl, $C_1$–$C_4$-alkoxy, $C_1$–$C_4$-alkylthio, $C_1$–$C_4$-haloalkyl, $C_1$–$C_4$-alkoxy-$C_1$–$C_4$-alkyl such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl and 1-ethoxy-1-methylethyl, in particular methoxyethyl and ethoxyethyl, $C_2$–$C_6$-alkenyl such as ethenyl and $C_3$–$C_6$-alkenyl,
$C_2$–$C_6$-alkenyloxy, in particular 1-methylethen-1-yloxy;
the phenyl or pyridyl group, which can both be unsubstituted or altogether can carry one to three radicals selected from the group consisting of
one to three radicals $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and
a radical —$NR^aR^b$, where $R^a$ is hydrogen,
$C_1$–$C_4$-alkyl, in particular methyl and ethyl,
$C_3$–$C_6$-alkenyl, in particular 2-propenyl and 2-butenyl, or
$C_3$–$C_6$-alkynyl, in particular 2-propynyl and 2-butynyl, and
$R^b$ is hydrogen,
$C_1$–$C_4$-alkyl, in particular methyl or ethyl,
$C_3$–$C_6$-alkenyl, in particular 2-propenyl or 2-butenyl, $C_3$–$C_6$-alkynyl, in particular 2-propynyl or 2-butynyl, $C_1$–$C_6$-acyl such as acetyl, propionyl, n-butyryl, 2-methylpropionyl, pentanoyl, 2-methylbutyryl, 3-methylbutyryl, 2,2-dimethylpropionyl, n-hexanoyl, 2-methylpentanoyl, 2-methylpentanoyl, 4-methylpentanoyl, 2,2-dimethylbutyryl, 2,3-dimethylbutyryl, 3,3-dimethylbutyryl and 2-ethylbutyryl, in particular acetyl and propionyl, or is
benzoyl, which in turn can be unsubstituted or can carry one to three radicals selected from the group consisting of nitro, cyano, halogen, preferably fluorine, chlorine and bromine, $C_1$–$C_4$-alkyl, preferably methyl, $C_1$–$C_4$-alkoxy, preferably methoxy and ethoxy, $C_1$–$C_4$-alkylthio, preferably methylthio, and $C_1$–$C_4$-halkyl, preferably trifluoromethyl.

Suitable salts of the O-(oximino)ethylcyclohexenone oxime ethers of the formula I are agriculturally utilizable salts, for example alkali metal salts, in particular the sodium or potassium salts, alkaline earth metal salts, in particular the calcium, magnesium or barium salts, the manganese, copper, zinc or iron salts, and ammonium, phosphonium, sulfonium or sulfoxonium salts, for example ammonium salts, tetraalkylammonium salts, benzyltrialylammonium salts, trialkylsulfonium salts or trialkylsulfoxonium salts.

Agriculturally utilizable esters are understood as meaning preferably the esters of $C_1$–$C_{10}$-fatty acids, in particular $C_1$–$C_6$-alkanecarboxylic acids such as methanecarboxylic acid (acetic acid), ethanecarboxylic acid (propionic acid), propanecarboxylic acid (butyric acid), 1-methylethanecarboxylic acid (isobutyric acid), butanecarboxylic acid, 1-methylpropanecarboxylic acid, 2-methylpropylcarboxylic acid, 1,1-dimethylethanecarboxylic acid, pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropanecarboxylic acid, 1-ethylpropanecarboxylic acid, benzoic acid and benzoic acids substituted by halogen, hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid.

The O-(oximino)ethylcyclohexenone oxime ethers I, their salts and esters are suitable, both as isomer mixtures and in the form of the pure isomers, as herbicides, in particular for controlling plant species from the grass family (Gramineae). In general, they are tolerable and thus selective in broad-leaved crops and in monocotyledonous plants which do not belong to the Gramineae. Some of the compounds I according to the invention are also suitable for the selective control of undesired grasses in Gramineae crops.

The selective action against broad-leaved weeds and grass weeds in crops such as wheat, rice, maize, soybeans and cotton occurs especially at low application rates.

The O-(oximino)ethylcyclohexenone oxime ethers I, their salts and esters, or the herbicidal compositions containing them, can be applied by spraying, atomizing, dusting, broadcasting or watering in the form of directly sprayable aqueous solutions, powders, suspensions, even high-percentage aqueous, oily or other suspensions or dispersions, emulsions, oil dispersions, pastes, dustlag compositions, broadcasting compositions or granules. The application forms depend on the intended uses; in each case if possible they should ensure the finest dispersion of the active compounds according to the invention.

The compounds I are generally suitable for the production of directly sprayable solutions, emulsions, pastes or oil dispersions. Suitable inert additives are mineral oil fractions of medium to high boiling point, such as kerosene or diesel oil, and also coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agents, adhesives, dispersants or emulsifiers and possibly concentrates consisting of solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of at least one compound I. The active compounds are employed here in a purity of from 90% to 100%, preferably from 95% to 100% (according to NMR spectrum).

The compounds I according to the invention can be formulated, for example, as follows:

I. 20 parts by weight of the compound No. 3.05 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 4.01 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 4.03 are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 15.09 are well mixed with 3 parts by weight of the sodium salt of diisobu-tylnaphthalene-α-sulfonic acid, 17 parts by weight of the sodium salt of a lignosulfonic acid from a sulfite waste liquor and 60 parts by weight of powdered silica gel and ground in a hamer mill. By finely dispersing the mixture in 20,000 parts by weight of water, a spray mixture is obtained which contains 0.1% by weight of the active compound.

V. 3 parts by weight of the active compound No. 9.04 are mixed with 97 parts by weight of finely divided kaolin. In this manner, a dusting composition is obtained which contains 3% by weight of the active compound.

VI. 20 parts by weight of the active compound No. 12.01 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that if possible the leaves of the sensitive crop plants are not affected, while the active compounds reach the leaves of undesired plants growing under them or the uncovered soil surface (post-directed, lay-by).

Depending on the target of control, time of year, target plants and growth stage, the application rates of active compound are from 0.001 to 3.0, preferably from 0.01 to 1.0, kg/ha of at least one active substance (a.s.) of the formula I.

Taking into account the variety of the application methods, the O-(oximino)ethylcyclohexenone oxime ethers I or compositions containing them can additionally be employed for the elimination of undesired plants in a further range of crop plants. Examples of suitable crops are the following:

*Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium praterise, Triticum aestivum, Triticum durum, Vicia faba, Vitis vinifera, Zea mays.*

To broaden the spectrum of action and to achieve synergistic effects, the O-(oximino)ethylcyclohexenone oxime ethers I can be mixed and applied jointly with numerous representatives of other herbicidal or growth-regulating active compound groups. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- and heteroaryloxyphenoxypropionic acids and their salts, esters and amides and others.

It may additionally be of use to apply the compounds I on their own or jointly in combination with other herbicides also additionally mixed with further crop protection agents, for example with agents for controlling pests or phytopathogenic fungi or bacteria. Also of interest is the miscibility with inorganic salt solutions which are employed for eliminating nutritional and trace element deficiencies. Non-phytotoxic oils and oil concentrates can also be added.

PREPARATION EXAMPLE

2-[1-{2-[2-(4-Chlorophenoxy)ethoximino]propoximino}butyl]-3-hydroxy-5-(2H-tetrahydrothiopyran-3-yl)-2-cyclohexen-1-one
(Compound No. 3.04)

A mixture of 1.00 g (3.56 mmol) of 3-hydroxy-2-butyryl-5-(2H-tetrahydrothiopyran-3-yl)-2-cyclohexen-1-one, 0.92 g (3.56 mmol) of O-{2-[2-(4-chlorophenoxy)ethoxyimino]propyl}hydroxylamine and 100 ml of methanol was stirred at 25° C. for 16 hours. The reaction mixture was then concentrated under reduced pressure, after which the residue was worked up to the product in a known manner. Yield: 65%

$^1$H-NMR(400 MHZ, in CDCl$_3$): δ [ppm]=4.20 (m, 2H), 4.40 (m, 2H), 6.85 (m, 2H), 7.20 (m, 2H) *)

*) Selected, representative signals

Precursor:

O-{2-[2-(4-Chlorophenoxy)ethoximino]propyl}hydroxylamine

A mixture of 5.30 g (24 mmol) of N-(2-oxo-1-propoxy)phthalimide {cf. Pharmazie 25, (1970) 400}, 4.50 g (24 mmol) of O-[2-(4-chlorophenoxy)ethyl]hydroxylamine (cf. EP-A 456,112) and 120 ml of methanol was stirred at 25° C. for 16 hours, after which it was concentrated at reduced pressure. The oil which remained (10 g) was treated with 100 ml of ethanolamine. After stirring at 40° C. for 4 hours, the mixture was stirred into water and then extracted three times with methylene chloride. The combined organic phases were washed with water, dried over sodium sulfate and concentrated. Yield: 79%

$^1$H-NMR (200 MHZ, in CDCl$_3$):

Main isomer (rel. content: 80%): δ [ppm]=1.35 (d, 3H), 1.80 (s, 3H), 4.00–4.30 (m, 2H), 4.15 (s, 2H), 4.65 (m, 1H), 5.45 (bs, 2H), 6.85 (m, 2H), 7.20 (m, 2H).

Secondary isomer (rel. content: 20%): δ [ppm]=1.30 (d, 3H), 1.95 (s, 3H), 4.00–4.30 (m, 2H), 4.15 (s, 2H), 4.65 (m, 1H), 5.45 (bs, 2H), 6.85 (m, 2H), 7.20 (m, 2H).

In the following Table I, further O-(oximino)ethylhydroxylamines III are shown which have been prepared or can be prepared in the same manner. Tables 2 to 24 contain O-(oximino)ethylcyclohexenone oxime ethers I according to the invention.

TABLE 1

$$H_2N-O-CH_2-\underset{R^2}{\overset{}{C}}=N-O-R^3$$

(III)

| No. | $R^2$ | $R^3$ | Phys. data ($^1$H-NMR [ppm]) |
|---|---|---|---|
| 1.01 | Methyl | 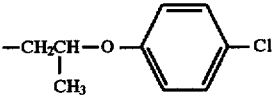 | Main isomer: 1.35 (d, 3H), 1.80 (s, 3H), 4.00–4.30 (m, 2H), 4.15 (s, 2H), 4.65 (m, 1H), 5.45 (bs, 2H), 6.85 (m, 2H), 7.20 (m, 2H)<br>Secondary isomer: 1.30 (d, 3H), 1.95 (s, 3H), 4.00–4.30 (m, 2H), 4.15 (s, 2H), 4.65 (m, 1H), 5.45 (bs, 2H), 6.85 (m, 2H), 7.20 (m, 2H) |
| 1.02 | Methyl | 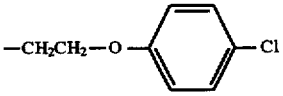 | Main isomer: 1.90 (s, 3H), 4.00–4.20 (m, 3H), 4.15 (s, 2H), 4.30–4.50 (m, 2H), 5.50 (bs, 2H), 6.85 (m, 2H), 7.20 (m, 2H)<br>Secondary isomer: 1.95 (s, 3H), 4.00–4.20 (m, 2H), 4.15 (s, 2H), 4.30–4.50 (m, 2H), 5.50 (bs, 2H), 6.85 (m, 2H), 7.20 (m, 2H) |
| 1.03 | Methyl | 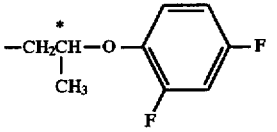 | Main isomer: 1.35 (d, 3H), 1.80 (s, 3H), 4.00–4.30 (m, 2H), 4.10 (s, 2H), 4.55 (m, 1H), 5.50 (bs, 2H), 6.70–7.10 (m, 3H),<br>Secondary isomer: 1.30 (d, 3H), 1.95 (s, 3H), 4.00–4.30 (m, 2H), 4.10 (s, 2H), 4.55 (m, 1H), 5.50 (bs, 2H), 6.70–7.10 (m, 3H)<br>$[\alpha]^{25}_D = -12.5$ (c = 1.0; MeOH) |
| 1.04 | Methyl | 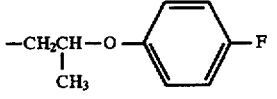 | Main isomer: 1.35 (d, 3H), 1.80 (s, 3H), 4.00–4.30 (m, 2H), 4.10 (s, 2H), 4.60 (m, 1H), 5.50 (bs, 2H), 6.90 (m, 4H),<br>Secondary isomer: 1.30 (d, 3H), 1.80 (s, 3H), 4.00–4.30 (m, 2H), 4.10 (s, 2H), 4.60 (m, 1H), 5.50 (bs, 2H), 6.90 (m, 4H) |
| 1.05 | Methyl | 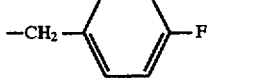 | Main isomer: 1.90 (s, 3H), 4.20 (s, 2H), 5.10 (s, 2H), 5.45 (bs, 2H), 7.05 (m, 2H), 7.35 (m, 2H),<br>Secondary isomer: 1.95 (s, 3H), 4.55 (s, 2H), 5.05 (s, 2H), 5.50 (bs, 2H), 7.05 (m, 2H), 7.35 (m, 2H) |
| 1.06 | Methyl | 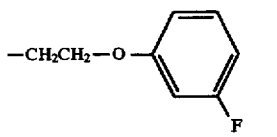 | Main isomer: 1.90 (s, 3H), 4.10–4.55 (m, 6H), 5.50 (bs, 2H), 6.70 (m, 3H), 7.20 (m, 1H)<br>Secondary isomer: 1.95 (s, 3H), 4.10–4.55 (m, 6H), 5.50 (bs, 2H), 6.70 (m, 3H), 7.20 (m, 1H) |
| 1.07 | Methyl | 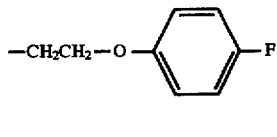 | Main isomer: 1.90 (s, 3H), 4.00–4.20 (m, 2H), 4.20 (s, 2H), 4.30–4.50 (m, 2H), 5.50 (bs, 2H), 6.85–7.05 (m, 4H)<br>Secondary isomer: 1.95 (s, 3H), 4.00–4.20 (m, 2H), 4.20 (s, 3H), 4.30–4.50 (m, 2H), 5.50 (bs, 2H), 6.85–7.05 (m, 4H) |
| 1.08 | Methyl | 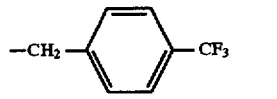 | Main isomer: 1.95 (s, 3H), 4.20 (s, 2H), 5.20 (s, 2H), 5.45 (bs, 2H), 7.45 (m, 2H), 7.55 (m, 2H)<br>Secondary isomer: 1.95 (s, 3H), 4.75 (s, 2H), 5.10 (s, 2H), 5.50 (bs, 2H), 7.45 (m, 2H), 7.55 (m, 2H) |
| 1.09 | Methyl | 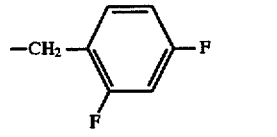 | Main isomer: 1.90 (s, 3H), 4.15 (s, 2H), 5.20 (s, 2H), 5.45 (bs, 2H), 6.80 (m, 2H), 7.40 (m, 1H)<br>Secondary isomer: 1.95 (s, 3H), 4.45 (s, 2H), 5.10 (s, 2H), 5.45 (bs, 2H), 6.80 (m, 2H), 7.40 (m, 1H) |
| 1.10 | Methyl | 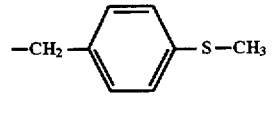 | Main isomer: 1.90 (s, 3H), 2.45 (s, 3H), 4.20 (s, 2H), 5.10 (s, 2H), 5.50 (bs, 2H), 7.20–7.30 (m, 4H)<br>Secondary isomer: 1.95 (s, 3H), 2.45 (s, 3H), 4.50 (s, 2H), 5.05 (s, 2H), 5.50 (m, 2H), 7.20–7.30 (m, 1H) |
| 1.11 | Methyl | 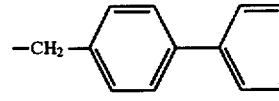 | Main isomer: 1.95 (s, 3H), 4.20 (s, 2H), 5.20 (s, 2H), 5.40 (bs, 2H), 7.20–7.70 (2m, 9H)<br>Secondary isomer: 1.95 (s, 3H), 4.70 (s, 2H), 5.20 (s, 2H), 5.40 (bs, 2H), 7.2–7.70 (2m, 9H) |

TABLE 1-continued $$H_2N-O-CH_2-C(R^2)=N-O-R^3$$

(III)

| No. | R² | R³ | Phys. data (¹H-NMR [ppm]) |
|---|---|---|---|
| 1.12 | Methyl | —CH₂—(C₆H₄)—O—C₆H₅ | Main isomer: 1.95 (s, 3H), 4.15 (s, 2H), 5.10 (s, 2H), 5.40 (bs, 2H), 6.90–7.40 (2m, 9H)<br>Secondary isomer: 1.95 (s, 3H), 4.65 (s, 2H), 5.05 (s, 2H), 5.40 (bs, 2H), 6.90–7.40 (2m, 9H) |
| 1.13 | Methyl | —CH₂—(2,4-Cl₂C₆H₃) | Main isomer: 1.95 (S, 3H), 4.20 (s, 2H), 5.20 (s, 2H), 5.45 (bs, 2H), 7.20–7.40 (m, 3H)<br>Secondary isomer: 1.95 (s, 3H), 4.80 (s, 2H), 5.15 (s, 2H), 5.50 (bs, 2H), 7.20–7.40 (m, 3H) |
| 1.14 | Methyl | —CH₂CH₃ | 1.30 (t, 3H), 1.90 (s, 3H), 4.10 (q, 2H), 4.15 (s, 2H), 5.50 (bs, 2H) |
| 1.15 | Methyl | —CH₂CH=CHCl | Main isomer: 1.90 (s, 3H), 4.15 (s, 2H), 4.55 (d, 2H), 5.50 (bs, 2H), 6.00–6.35 (m, 2H)<br>Secondary isomer: 1.95 (s, 3H), 4.45 (s, 2H), 4.50 (d, 2H), 5.50 (bs, 2H), 6.00–6.35 (m, 2H) |
| 1.16 | n-Butyl | —CH₂CH=CHCl | Main isomer: 2.25 (t, 2H), 5.50 (bs, 2H), 6.00–6.35 (m, 2H)<br>Secondary isomer: 2.35 (t, 2H), 5.50 (bs, 2H), 6.00–6.35 (m, 2H) |
| 1.17 | n-Butyl | —CH₂CH(CH₃)—O—(4-ClC₆H₄) | 2.25 (t, 2H), 5.50 (bs, 2H), 6.85 (m, 2H), 7.20 (m, 2H) |

TABLE 2

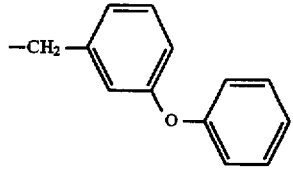

I  (R² = CH₃, R³ = —CH₂CH(CH₃)—O—(4-ClC₆H₄))

| No. | R¹ | R⁴ | Phys. data (¹H-NMR [ppm]) |
|---|---|---|---|
| 2.01 | Ethyl | 2H-Tetrahydropyran-3-yl | |
| 2.02 | n-Propyl | 2H-Tetrahydropyran-3-yl | |
| 2.03 | Ethyl | 2H-Tetrahydrothiopyran-3-yl | |
| 2.04 | n-Propyl | 2H-Tetrahydrothiopyran-3-yl | 4.10–4.30 (m, 2H), 6.85 (m, 2H), 7.20 (m, 2H) |
| 2.05 | Ethyl | 2H-Tetrahydropyran-4-yl | 4.00 (m, 2H), 4.10–4.30 (m, 2H), 6.85 (m, 2H), 7.20 (m, 2H) |
| 2.06 | n-Propyl | 2H-Tetrahydropyran-4-yl | |
| 2.07 | Ethyl | 2H-Tetrahydropyran-4-yl | |
| 2.08 | Ethyl | 1-Methylthiocyclo-prop-1-yl | |
| 2.09 | n-Propyl | 2-(Ethylthio)prop-1-yl | 4.10–4.30 (m, 2H), 6.85 (m, 2H), 7.20 (m, 2H) |
| 2.10 | Ethyl | 2-(4-Fluorophenylthio)-ethyl | |
| 2.11 | n-Propyl | 1,3-Dimethylpyrazol-5-yl | |
| 2.12 | n-Propyl | 3-Isopropylisoxazol-5-yl | |
| 2.13 | n-Propyl | N-(Ethylsulfonyl)-N-methylaminomethyl | |

TABLE 3

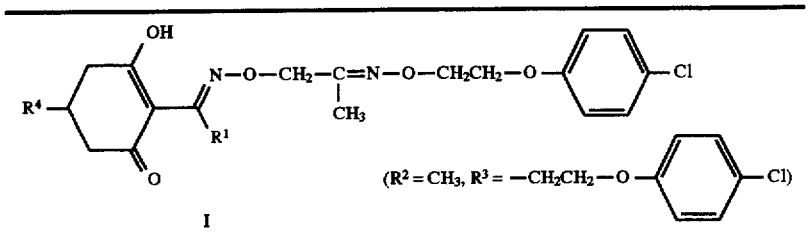

| No. | R¹ | R⁴ | Phys. data (¹H-NMR [ppm]) |
|---|---|---|---|
| 3.01 | Ethyl | 2H-Tetrahydropyran-3-yl | |
| 3.02 | n-Propyl | 2H-Tetrahydropyran-3-yl | |
| 3.03 | Ethyl | 2H-Tetrahydrothiopyran-3-yl | |
| 3.04 | n-Propyl | 2H-Tetrahydrothiopyran-3-yl | 4.20 (m, 2H), 4.40 (m, 2H), 6.85 (m, 2H), 7.20 (m, 2H) |
| 3.05 | Ethyl | 2H-Tetrahydropyran-4-yl | 4.00 (m, 2H), 4.20 (m, 2H), 4.40 (m, 2H), 6.85 (m, 2H), 7.20 (m, 2H) |
| 3.06 | n-Propyl | 2H-Tetrahydropyran-4-yl | |
| 3.07 | Ethyl | 2,4,6-Trimethylphenyl | |
| 3.08 | Ethyl | 1-Methylthiocycloprop-1-yl | |
| 3.09 | n-Propyl | 2-(Ethylthio)propyl | 4.15 (m, 2H), 4.35 (m, 2H), 6.85 (m, 2H), 7.20 (m, 2H) |
| 3.10 | Ethyl | 2-(4-Fluorophenylthio)-ethyl | |
| 3.11 | n-Propyl | 1,3-Dimethylpyrazol-5-yl | |
| 3.12 | n-Propyl | 3-Isopropylisoxazol-5-yl | |
| 3.13 | n-Propyl | N-(Ethylsulfonyl)-N-methylaminomethyl | |

TABLE 4

*) R-configuration

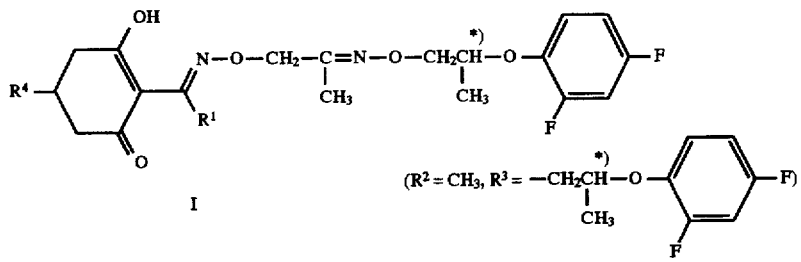

| No. | R¹ | R⁴ | Phys. data (¹H-NMR [ppm]) |
|---|---|---|---|
| 4.01 | Ethyl | 2H-Tetrahydropyran-3-yl | 3.90 (m, 2H), 4.10–4.90 (m, 2H), 6.70–7.10 (m, 3H)<br>$[\alpha]_D^{25} = -10.9$ (c = 1.0; methanol) |
| 4.02 | n-Propyl | 2H-Tetrahydropyran-3-yl | |
| 4.03 | Ethyl | 2H-Tetrahydrothiopyran-3-yl- | 4.10–4.40 (m, 2H), 6.70–7.10 (m, 3H)<br>$[\alpha]_D^{25} = -11.1$ (c = 1.0; methanol) |
| 4.04 | n-Propyl | 2H-Tetrahydrothiopyran-3-yl | 4.10–4.40 (m, 2H), 6.70–7.10 (m, 3H)<br>$[\alpha]_D^{25} = -10.8$ (c = 1.0; methanol) |
| 4.05 | Ethyl | 2H-Tetrahydropyran-4-yl | 4.00 (m, 2H), 4.10–4.40 (m, 2H), 6.70–7.10 (m, 3H)<br>$[\alpha]_D^{25} = -10.9$ (c = 1.0; methanol) |
| 4.06 | n-Propyl | 2H-Tetrahydropyran-4-yl | |
| 4.07 | Ethyl | 2,4,6-Trimethylphenyl | |
| 4.08 | Ethyl | 1-Methylthiocycloprop-1-yl | |
| 4.09 | n-Propyl | 2-(Ethylthio)prop-1-yl | 4.05–4.35 (m, 2H), 6.70–7.10 (m, 3H)<br>$[\alpha]_D^{25} = -6.8$ (c = 1.0; methanol) |
| 4.10 | Ethyl | 2-(4-Fluorophenylthio)-ethyl | |
| 4.11 | n-Propyl | 1,3-Dimethylpyrazol-5-yl | |
| 4.12 | n-Propyl | 3-Isopropylisoxazol-5-yl | |
| 4.13 | n-Propyl | N-(Ethylsulfonyl)-N-methylaminomethyl | |

TABLE 5

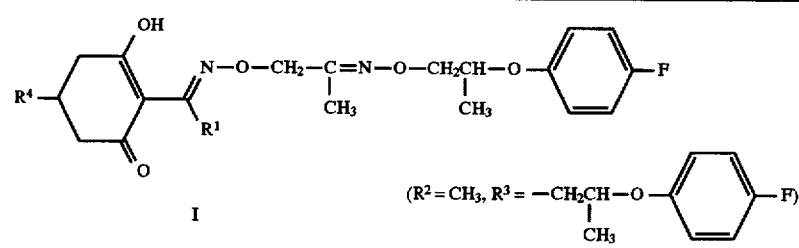

| No. | R¹ | R⁴ | Phys. data (¹H-NMR [ppm]) |
|---|---|---|---|
| 5.01 | Ethyl | 2H-Tetrahydropyran-3-yl | |
| 5.02 | n-Propyl | 2H-Tetrahydropyran-3-yl | |
| 5.03 | Ethyl | 2H-Tetrahydrothiopyran-3-yl | |
| 5.04 | n-Propyl | 2H-Tetrahydrothiopyran-3-yl | 4.10–4.30 (m, 2H), 6.85–7.00 (m, 4H) |
| 5.05 | Ethyl | 2H-Tetrahydropyran-4-yl | 4.00 (m, 2H), 4.10–4.30 (m, 2H), 6.85–7.00 (m, 4H) |
| 5.06 | n-Propyl | 2H-Tetrahydropyran-4-yl | |
| 5.07 | Ethyl | 2,4,6-Trimethylphenyl | |
| 5.08 | Ethyl | 1-Methylthiocycloprop-1-yl | |
| 5.09 | n-Propyl | 2-(Ethylthio)prop-1-yl | 4.10–4.30 (m, 2H), 6.85–7.00 (m, 4H) |
| 5.10 | Ethyl | 2-(4-Fluorophenylthio)-ethyl | |
| 5.11 | n-Propyl | 1,3-Dimethylpyrazol-5-yl | |
| 5.12 | n-Propyl | 3-Isopropylisoxazol-5-yl | |
| 5.13 | n-Propyl | N-(Ethylsulfonyl)-N-methylaminomethyl | |

TABLE 6

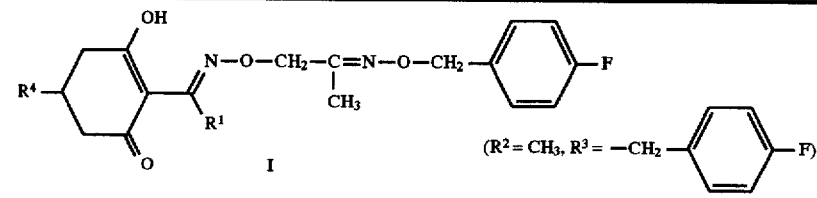

| No. | R¹ | R⁴ | Phys. data (¹H-NMR [in ppm]) |
|---|---|---|---|
| 6.01 | Ethyl | 2H-Tetrahydropyran-3-yl | |
| 6.02 | n-Propyl | 2H-Tetrahydropyran-3-yl | |
| 6.03 | Ethyl | 2H-Tetrahydrothiopyran-3-yl | |
| 6.04 | n-Propyl | 2H-Tetrahydrothiopyran-3-yl | 4.50 (s, 2H), 5.10 (s, 2H), 7.05 (m, 2H), 7.35 (m, 2H) |
| 6.05 | Ethyl | 2H-Tetrahydropyran-4-yl | 4.05 (m, 2H), 4.50 (s, 2H), 5.10 (s, 2H), 7.05 (m, 2H), 7.35 (m, 2H) |
| 6.06 | n-Propyl | 2H-Tetrahydropyran-4-yl | |
| 6.07 | Ethyl | 2,4,6-Trimethylphenyl | |
| 6.08 | Ethyl | 1-Methylthiocycloprop-1-yl | |
| 6.09 | n-Propyl | 2-(Ethylthio)prop-1-yl | 4.50 (s, 2H), 5.10 (s, 2H), 7.05 (m, 2H), 7.35 (m, 2H) |
| 6.10 | Ethyl | 2-(4-Fluorophenylthio)-ethyl | |
| 6.11 | n-Propyl | 1,3-Dimethylpyrazol-5-yl | |
| 6.12 | n-Propyl | 3-Isopropylisoxazol-5-yl | |
| 6.13 | n-Propyl | N-(Ethylsulfonyl)-N-methylaminomethyl | |

TABLE 7

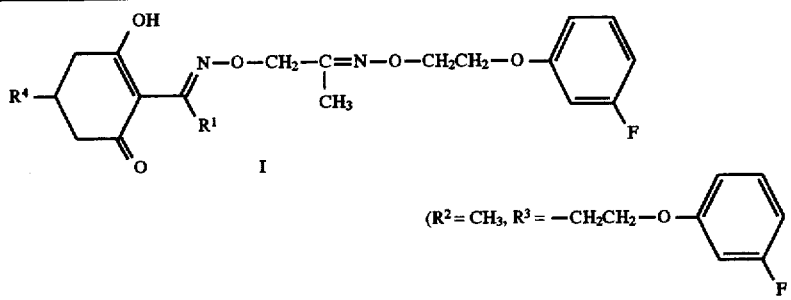

($R^2$ = $CH_3$, $R^3$ = —$CH_2CH_2$—O—⟨3-F-phenyl⟩)

| No. | $R^1$ | $R^4$ | Phys. data ($^1$H-NMR [in ppm]) |
|---|---|---|---|
| 7.01 | Ethyl | 2H-Tetrahydropyran-3-yl | 3.90 (m, 2H), 4.15–4.25 (m, 2H), 4.35–4.45 (m, 2H), 6.65–6.80 (m, 3H), 7.15–7.25 (m, 1H) |
| 7.02 | n-Propyl | 2H-Tetrahydropyran-3-yl | |
| 7.03 | Ethyl | 2H-Tetrahydrothiopyran-3-yl | 4.15–4.30 (m, 2H), 4.35–4.45 (m, 2H), 6.70–6.80 (m, 3H), 7.15–7.25 (m, 1H) |
| 7.04 | n-Propyl | 2H-Tetrahydrothiopyran-3-yl | 4.15–4.25 (m, 2H), 4.35–4.45 (m, 2H), 6.65–6.80 (m, 3H), 7.15–7.25(m, 1H) |
| 7.05 | Ethyl | 2H-Tetrahydropyran-4-yl | 4.00 (m, 2H), 4.15–4.25 (m, 2H), 4.35–4.45 (m, 2H) 6.65–6.80 (m, 3H), 7.15–7.25 (m, 1H) |
| 7.06 | n-Propyl | 2H-Tetrahydropyran-4-yl | |
| 7.07 | Ethyl | 2,4,6-Trimethylphenyl | |
| 7.08 | Ethyl | 1-Methylthiocyclo-prop-1-yl | |
| 7.09 | n-Propyl | 2-(Ethylthio)prop-1-yl | 4.10–4.25(m, 2H), 4.30–4.45 (m, 2H), 6.65–6.80 (m, 3H), 7.15–7.25 (m, 1H) |
| 7.10 | Ethyl | 2-(4-Fluorophenylthio)-ethyl | |
| 7.11 | n-Propyl | 1,3-Dimethylpyrazol-5-yl | |
| 7.12 | n-Propyl | 3-Isopropylisoxazol-5-yl | |
| 7.13 | n-Propyl | N-(Ethylsulfonyl)-N-methylaminomethyl | |

TABLE 8

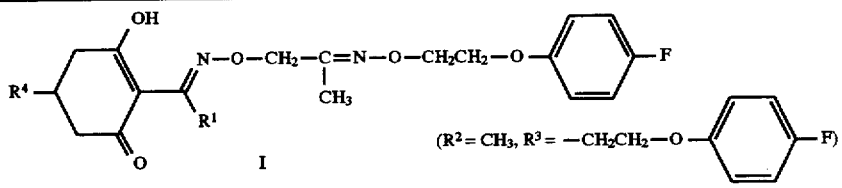

($R^2$ = $CH_3$, $R^3$ = —$CH_2CH_2$—O—⟨4-F-phenyl⟩)

| No. | $R^1$ | $R^4$ | Phys. data ($^1$H-NMR [in ppm]) |
|---|---|---|---|
| 8.01 | Ethyl | 2H-Tetrahydropyran-3-yl | 3.90 (m, 2H), 4.15–4.25 (m, 2H), 4.40 (m, 2H), 6.85 (m, 2H), 6.95 (m, 2H) |
| 8.02 | n-Propyl | 2H-Tetrahydropyran-3-yl | |
| 8.03 | Ethyl | 2H-Tetrahydrothiopyran-3-yl | 4.15–4.25 (m, 2H), 4.40 (m, 2H), 6.85 (m, 2H), 6.95 (m, 2H) |
| 8.04 | n-Propyl | 2H-Tetrahydrothiopyran-3-yl | 4.15–4.25 (m, 2H), 4.40 (m, 2H), 6.85 (m, 2H), 6.95 (m, 2H) |
| 8.05 | Ethyl | 2H-Tetrahydropyran-4-yl | 4.00 (m, 2H), 4.15–4.25 (m, 2H), 4.40 (m, 2H), 6.85 (m, 2H), 6.95–7.25 (m, 2H) |
| 8.06 | n-Propyl | 2H-Tetrahydropyran-4-yl | |
| 8.07 | Ethyl | 2,4,6-Trimethylphenyl | |
| 8.08 | Ethyl | 1-Methylthiocyclo-prop-1-yl | |
| 8.09 | n-Propyl | 2-(Ethylthio)prop-1-yl | 4.15–4.25 (m, 2H), 4.40 (m, 2H), 6.85 (m, 2H), 6.95 (m, 2H) |
| 8.10 | Ethyl | 2-(4-Fluorophenylthio)-ethyl | |
| 8.11 | n-Propyl | 1,3-Dimethylpyrazol-5-yl | |
| 8.12 | n-Propyl | 3-Isopropylisoxazol-5-yl | |
| 8.13 | n-Propyl | N-(Ethylsulfonyl)-N-methylaminomethyl | |

TABLE 9

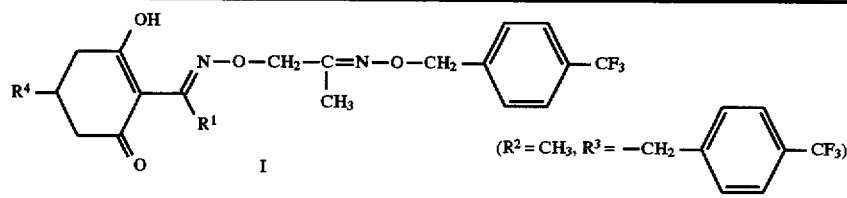

($R^2 = CH_3$, $R^3 = -CH_2-\text{C}_6\text{H}_4-CF_3$)

| No. | $R^1$ | $R^4$ | Phys. data ($^1$H-NMR [in ppm]) |
|---|---|---|---|
| 9.01 | Ethyl | 2H-Tetrahydropyran-3-yl | 3.90 (m, 2H), 4.50 (s, 2H), 5.20 (s, 2H), 7.45 (m, 2H), 7.60 (m, 2H) |
| 9.02 | n-Propyl | 2H-Tetrahydropyran-3-yl | |
| 9.03 | Ethyl | 2H-Tetrahydrothiopyran-3-yl | 4.50 (s, 2H), 5.20 (s, 2H), 7.45 (m, 2H), 7.60 (m, 2H) |
| 9.04 | n-Propyl | 2H-Tetrahydrothiopyran-3-yl | 4.50 (s, 2H), 5.20 (s, 2H), 7.45 (m, 2H), 7.60 (m, 2H) |
| 9.05 | Ethyl | 2H-Tetrahydropyran-4-yl | 4.00 (m, 2H), 4.50 (s, 2H), 5.20 (m, 2H), 7.45 (m, 2H), 7.60 (m, 2H) |
| 9.06 | n-Propyl | 2H-Tetrahydropyran-4-yl | |
| 9.07 | Ethyl | 2,4,6-Trimethylphenyl | |
| 9.08 | Ethyl | 1-Methylthiocyclo-prop-1-yl | |
| 9.09 | n-Propyl | 2-(Ethylthio)prop-1-yl | 4.50 (s, 2H), 5.20 (s, 2H), 7.45 (m, 2H), 7.60 (m, 2H) |
| 9.10 | Ethyl | 2-(4-Fluorophenylthio)-ethyl | |
| 9.11 | n-Propyl | 1,3-Dimethylpyrazol-5-yl | |
| 9.12 | n-Propyl | 3-Isopropylisoxazol-5-yl | |
| 9.13 | n-Propyl | N-(Ethylsulfonyl)-N-methylaminomethyl | |

TABLE 10

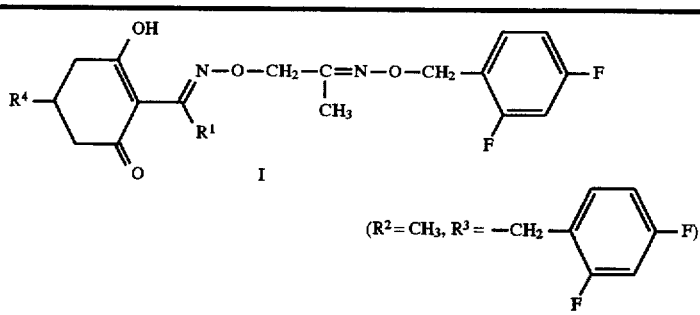

($R^2 = CH_3$, $R^3 = -CH_2-\text{C}_6\text{H}_3\text{F}_2$)

| No. | $R^1$ | $R^4$ | Phys. data ($^1$H-NMR [in ppm]) |
|---|---|---|---|
| 10.01 | Ethyl | 2H-Tetrahydropyran-3-yl | 3.90 (m, 2H), 4.55 (s, 2H), 5.15 (s, 2H), 6.85 (m, 2H), 7.40 (m, 1H) |
| 10.02 | n-Propyl | 2H-Tetrahydropyran-3-yl | |
| 10.03 | Ethyl | 2H-Tetrahydrothiopyran-3-yl | 4.55 (s, 2H), 5.15 (s, 2H), 6.85 (m, 2H), 7.40 (m, 2H) |
| 10.04 | n-Propyl | 2H-Tetrahydrothiopyran-3-yl | 4.55 (s, 2H), 5.15 (s, 2H), 6.85 (m, 2H), 7.40 (m, 1H) |
| 10.05 | Ethyl | 2H-Tetrahydropyran-4-yl | 4.00 (m, 2H), 4.55 (s, 2H), 5.15 (s, 2H), 6.85 (m, 2H), 7.40 (m, 1H) |
| 10.06 | n-Propyl | 2H-Tetrahydropyran-4-yl | |
| 10.07 | Ethyl | 2,4,6-Trimethylphenyl | |
| 10.08 | Ethyl | 1-Methylthiocyclo-prop-1-yl | |
| 10.09 | n-Propyl | 2(Ethylthio)prop-1-yl | 4.55 (s, 2H), 5.15 (s, .2H), 6.85 (m, 2H), 7.40 (m, 1H) |
| 10.10 | Ethyl | 2-(4-Fluorophenylthio)-ethyl | |
| 10.11 | n-Propyl | 1,3-Dimethylpyrazol-5-yl | |
| 10.12 | n-Propyl | 3-Isopropylisoxazol-5-yl | |
| 10.13 | n-Propyl | N-(Ethylsulfonyl)-N-methylaminomethyl | |

TABLE 11

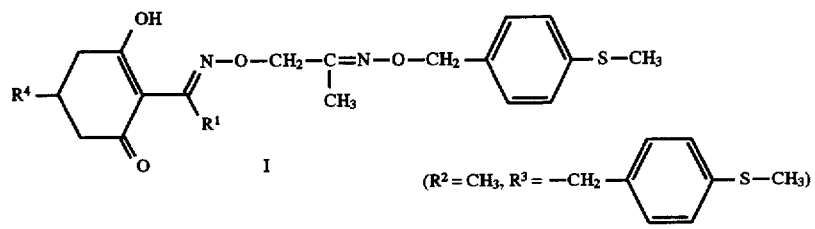

| No. | R¹ | R⁴ | Phys. data ($^1$H-NMR [in ppm]) |
|---|---|---|---|
| 11.01 | Ethyl | 2H-Tetrahydropyran-3-yl | |
| 11.02 | n-Propyl | 2H-Tetrahydropyran-3-yl | |
| 11.03 | Ethyl | 2H-Tetrahydrothiopyran-3-yl | |
| 11.04 | n-Propyl | 2H-Tetrahydrothiopyran-3-yl | |
| 11.05 | Ethyl | 2H-Tetrahydropyran-4-yl | |
| 11.06 | n-Propyl | 2H-Tetrahydropyran-4-yl | |
| 11.07 | Ethyl | 2,4,6-Trimethylphenyl | |
| 11.08 | Ethyl | 1-Methylthiocyclo-prop-1-yl | |
| 11.09 | n-Propyl | 2-(Ethylthio)prop-1-yl | 4.50 (s, 2H), 5.20 (s, 2H), 7.20–7.30 (m, 4H) |
| 11.10 | Ethyl | 2-(4-Fluorophenylthio)-ethyl | |
| 11.11 | n-Propyl | 1,3-Dimethylpyrazol-5-yl | |
| 11.12 | n-Propyl | 3-Isopropylisoxazol-5-yl | |
| 11.13 | n-Propyl | N-(Ethylsulfonyl)-N-methylaminomethyl | |

TABLE 12

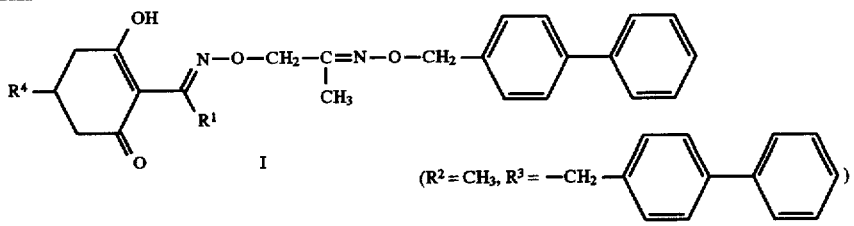

| No. | R¹ | R⁴ | Phys. data ($^1$H-NMR [in ppm]) |
|---|---|---|---|
| 12.01 | Ethyl | 2H-Tetrahydropyran-3-yl | 3.90 (m, 2H), 4.50 (s, 2H), 5.20 (s, 2H), 7.20–7.70 (3m, 9H) |
| 12.02 | n-Propyl | 2H-Tetrahydropyran-3-yl | |
| 12.03 | Ethyl | 2H-Tetrahydrothiopyran-3-yl | 4.50 (s, 2H), 5.20 (s, 2H), 7.20–7.10 (3m, 9H) |
| 12.04 | n-Propyl | 2H-Tetrahydrothiopyran-3-yl | 4.50 (s, 2H), 5.20 (s, 2H), 7.20–7.70 (3m, 9H) |
| 12.05 | Ethyl | 2H-Tetrahydropyran-4-yl | |
| 12.06 | n-Propyl | 2H-Tetrahydropyran-4-yl | |
| 12.07 | Ethyl | 2,4,6-Trimethylphenyl | |
| 12.08 | Ethyl | 1-Methylthiocyclo-prop-1-yl | |
| 12.09 | n-Propyl | 2-(Ethylthio)prop-1-yl | 4.50 (s, 2H), 5.20 (s, 2H), 7.20–7.70 (3m, 9H) |
| 12.10 | Ethyl | 2-(4-Fluorophenylthio)-ethyl | |
| 12.11 | n-Propyl | 1,3-Dimethylpyrazol-5-yl | |
| 12.12 | n-Propyl | 3-Isopropylisoxazol-5-yl | |
| 12.13 | n-Propyl | N-(Ethylsulfonyl)-N-methylaminomethyl | |

TABLE 13

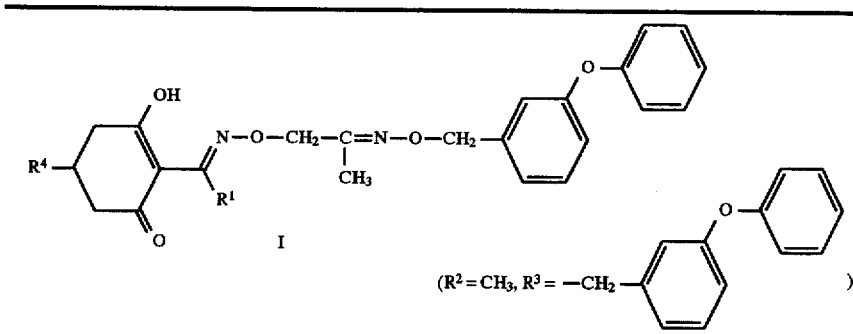

($R^2 = CH_3$, $R^3 = -CH_2$-phenyl-O-phenyl)

| No. | $R^1$ | $R^4$ | Phys. data ($^1$H-NMR [in ppm]) |
|---|---|---|---|
| 13.01 | Ethyl | 2H-Tetrahydropyran-3-yl | 3.90 (m, 2H), 4.50 (s, 2H), 5.15 (s, 2H), 6.90–7.40 (m, 9H) |
| 13.02 | n-Propyl | 2H-Tetrahydropyran-3-yl | |
| 13.03 | Ethyl | 2H-Tetrahydrothiopyran-3-yl | 4.50 (s, 2H), 5.15 (s, 2H), 6.90–7.40 (m, 9H) |
| 13.04 | n-Propyl | 2H-Tetrahydrothiopyran-3-yl | 4.50 (s, 2H), 5.15 (s, 2H), 6.90–7.40 (m, 9H) |
| 13.05 | Ethyl | 2H-Tetrahydropyran-4-yl | 4.00 (m, 2H), 4.50 (s, 2H), 5.15 (s, 2H), 6.90–7.40 (m, 9H) |
| 13.06 | n-Propyl | 2H-Tetrahydropyran-4-yl | |
| 13.07 | Ethyl | 2,4,6-Trimethylphenyl | |
| 13.08 | Ethyl | 1-Methylthiocyclo-prop-1-yl | |
| 13.09 | n-Propyl | 2-(Ethylthio)prop-1-yl | 4.50 (s, 2H), 5.15 (s, 2H), 6.90–7.40 (m, 9H) |
| 13.10 | Ethyl | 2-(4-Fluorophenylthio)-ethyl | |
| 13.11 | n-Propyl | 1,3-Dimethylpyrazol-5-yl | |
| 13.12 | n-Propyl | 3-Isopropylisoxazol-5-yl | |
| 13.13 | n-Propyl | N-(Ethylsulfonyl)-N-methylaminomethyl | |

TABLE 14

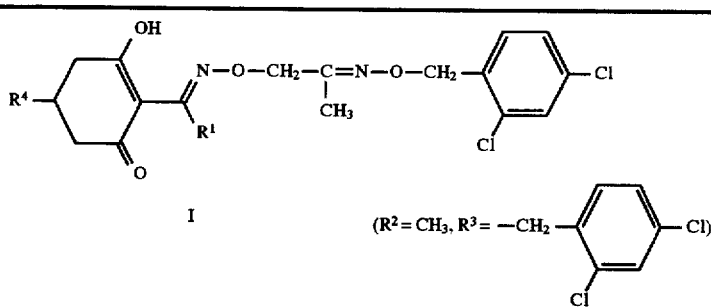

($R^2 = CH_3$, $R^3 = -CH_2$-(2,4-dichlorophenyl))

| No. | $R^1$ | $R^4$ | Phys. data ($^1$H-NMR [in ppm]) |
|---|---|---|---|
| 14.01 | Ethyl | 2H-Tetrahydropyran-3-yl | 3.90 (m, 2H), 4.50 (s, 2H), 5.20 (s, 2H), 7.20–7.40 (m, 3H) |
| 14.02 | n-Propyl | 2H-Tetrahydropyran-3-yl | |
| 14.03 | Ethyl | 2H-Tetrahydrothiopyran-3-yl | 4.50 (s, 2H), 5.20 (s, 2H), 7.20–7.40 (m, 3H) |
| 14.04 | n-Propyl | 2H-Tetrahydrothiopyran-3-yl | 4.50 (s, 2H), 5.20 (s, 2H), 7.20–7.40 (m, 3H) |
| 14.05 | Ethyl | 2H-Tetrahydropyran-4-yl | 4.00 (m, 2H), 4.50 (s, 2H), 5.20 (s, 2H), 7.20–7.40 (m, 3H) |
| 14.06 | n-Propyl | 2H-Tetrahydropyran-4-yl | |
| 14.07 | Ethyl | 2,4,6-Trimethylphenyl | |
| 14.08 | Ethyl | 1-Methylthiocyclo-prop-1-yl | |
| 14.09 | n-Propyl | 2-(Ethylthio)prop-1-yl | 4.50 (s, 2H), 5.20 (s, 2H), 7.20–7.40 (m, 3H) |
| 14.10 | Ethyl | 2-(4-Fluorophenylthio)-ethyl | |
| 14.11 | n-Propyl | 1,3-Dimethylpyrazol-5-yl | |
| 14.12 | n-Propyl | 3-Isopropylisoxazol-5-yl | |
| 14.13 | n-Propyl | N-(Ethylsulfonyl)-N-methylaminomethyl | |

TABLE 15

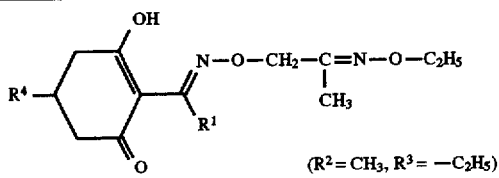

($R^2 = CH_3$, $R^3 = -C_2H_5$)

I

| No. | $R^1$ | $R^4$ | Phys. data ($^1$H-NMR [in ppm]) |
|---|---|---|---|
| 15.01 | Ethyl | 2H-Tetrahydropyran-3-yl | 1.90 (s, 3H), 3.90 (m, 2H), 4.15 (m, 2H), 4.50 (s, 2H) |
| 15.02 | n-Propyl | 2H-Tetrahydropyran-3-yl | 1.90 (s, 3H), 3.90 (m, 2H), 4.15 (m, 2H), 4.50 (s, 2H) |
| 15.03 | Ethyl | 2H-Tetrahydrothiopyran-3-yl | 1.90 (s, 3H), 4.15 (m, 2H), 4.50 (s, 2H) |
| 15.04 | n-Propyl | 2H-Tetrahydrothiopyran-3-yl | 1.90 (s, 3H), 4.15 (m, 2H), 4.50 (s, 2H) |
| 15.05 | Ethyl | 2H-Tetrahydropyran-4-yl | 1.90 (s, 3H), 4.00 (m, 2H), 4.15 (m, 2H), 4.50 (s, 2H) |
| 15.06 | n-Propyl | 2H-Tetrahydropyran-4-yl | 1.90 (s, 3H), 4.00 (m, 2H), 4.15 (m, 2H), 4.50 (s, 2H) |
| 15.07 | Ethyl | 2,4,6-Trimethylphenyl | |
| 15.08 | Ethyl | 1-Methylthiocyclo-prop-1-yl | |
| 15.09 | n-Propyl | 2-(Ethylthio)prop-1-yl | 1.90 (s, 3H), 4.15 (m, 2H), 4.50 (s, 2H) |
| 15.10 | Ethyl | 2-(4-Fluorophenylthio)-ethyl | |
| 15.11 | n-Propyl | 1,3-Dimethylpyrazol-5-yl | |
| 15.12 | n-Propyl | 3-Isopropylisoxazol-5-yl | |
| 15.13 | n-Propyl | N-(Ethylsulfonyl)-N-methylaminomethyl | |

TABLE 16

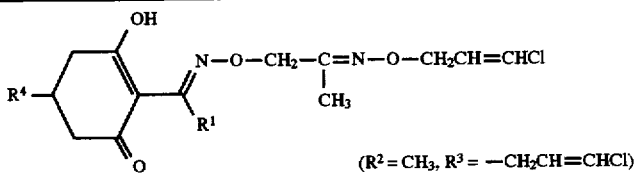

($R^2 = CH_3$, $R^3 = -CH_2CH=CHCl$)

I

| No. | $R^1$ | $R^4$ | Phys. data ($^1$H-NMR [in ppm]) |
|---|---|---|---|
| 16.01 | Ethyl | 2H-Tetrahydropyran-3-yl | 1.90 (s, 3H), 3.90 (m, 2H), 4.50 (s, 2H), 4.55 (m, 2H), 6.00–6.35 (m, 2H) |
| 16.02 | n-Propyl | 2H-Tetrahydropyran-3-yl | 1.90 (s, 3H), 3.90 (m, 2H), 4.50 (m, 2H), 4.55 (m, 2H), 6.00–6.35 (m, 2H) |
| 16.03 | Ethyl | 2H-Tetrahydrothiopyran-3-yl | 1.90 (s, 3H), 4.50 (s, 2H), 4.55 (m, 2H), 6.00–6.35 (m, 2H) |
| 16.04 | n-Propyl | 2H-Tetrahydrothiopyran-3-yl | 1.90 (s, 3H), 4.50 (s, 2H), 4.55 (m, 2H), 6.00–6.35 (m, 2H) |
| 16.05 | Ethyl | 2H-Tetrahydropyran-4-yl | 1.90 (s, 3H), 4.00 (m, 2H), 4.50 (s, 2H), 4.55 (m, 2H), 6.00–6.35 (m, 2H) |
| 16.06 | n-Propyl | 2H-Tetrahydropyran-4-yl | 1.90 (s, 3H), 4.00 (m, 2H), 4.50 (s, 2H), 4.55 (m, 2H), 6.00–6.35 (m, 2H) |
| 16.07 | Ethyl | 2,4,6-Trimethylphenyl | |
| 16.08 | Ethyl | 1-Methylthiocyclo-prop-1-yl | |
| 16.09 | n-Propyl | 2-(Ethylthio)prop-1-yl | 1.90 (s, 3H), 4.50 (,s, 2H), 4.55 (m, 2H), 6.00–6.35 (m, 2H) |
| 16.10 | Ethyl | 2-(4-Fluorophenylthio)-ethyl | |
| 16.11 | n-Propyl | 1,3-Dimethylpyrazol-5-yl | |
| 16.12 | n-Propyl | 3-Isopropylisoxazol-5-yl | |
| 16.13 | n-Propyl | N-(Ethylsulfonyl)-N-methylaminomethyl | |

TABLE 17

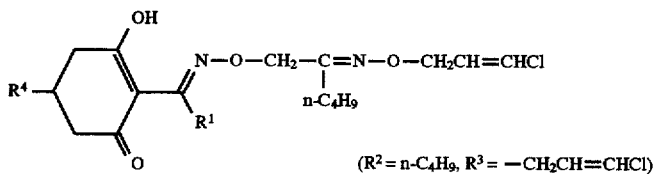

$(R^2 = n\text{-}C_4H_9, R^3 = -CH_2CH=CHCl)$

I

| No. | $R^1$ | $R^4$ | Phys. data ($^1$H-NMR [in ppm]) |
|---|---|---|---|
| 17.01 | Ethyl | 2H-Tetrahydropyran-3-yl | 3.90 (m, 2H), 6.00–6.35 (m, 2H) |
| 17.02 | n-Propyl | 2H-Tetrahydropyran-3-yl | 3.90 (m, 2H), 6.00–6.35 (m, 2H) |
| 17.03 | Ethyl | 2H-Tetrahydrothiopyran-3-yl | 6.00–6.35 (m, 2H) |
| 17.04 | n-Propyl | 2H-Tetrahydrothiopyran-3-yl | 6.00–6.35 (m, 2H) |
| 17.05 | Ethyl | 2H-Tetrahydropyran-4-yl | 4.00 (m, 2H), 6.00–6.35 (m, 2H) |
| 17.06 | n-Propyl | 2H-Tetrahydropyran-4-yl | 4.00 (m, 2H), 6.00–6.35 (m, 2H) |
| 17.07 | Ethyl | 2,4,6-Trimethylphenyl | |
| 17.08 | Ethyl | 1-Methylthiocyclo-prop-1-yl | |
| 17.09 | n-Propyl | 2-(Ethylthio)prop-1-yl | |
| 17.10 | Ethyl | 2-(4-Fluorophenylthio)-ethyl | |
| 17.11 | n-Propyl | 1,3-Dimethylpyrazol-5-yl | |
| 17.12 | n-Propyl | 3-Isopropylisoxazol-5-yl | |
| 17.13 | n-Propyl | N-(Ethylsulfonyl)-N-methylaminomethyl | |

TABLE 18

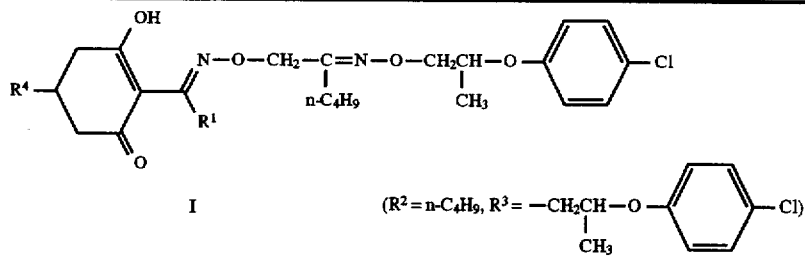

$(R^2 = n\text{-}C_4H_9, R^3 = -CH_2CH-O-\phenyl-Cl)$
$\quad\quad\quad\quad\quad\quad\quad\quad\quad\; |$
$\quad\quad\quad\quad\quad\quad\quad\quad\; CH_3$

I

| No. | $R^1$ | $R^4$ | Phys. data ($^1$H-NMR [in ppm]) |
|---|---|---|---|
| 18.01 | Ethyl | 2H-Tetrahydropyran-3-yl | 3.90 (m, 2H), 6.85 (m, 2H), 7.20 (m, 2H) |
| 18.02 | n-Propyl | 2H-Tetrahydropyran-3-yl | 3.90 (m, 2H), 6.85 (m, 2H), 7.20 (m, 2H) |
| 18.03 | Ethyl | 2H-Tetrahydrothiopyran-3-yl | 6.85 (m, 2H), 7.20 (m, 2H) |
| 18.04 | n-Propyl | 2H-Tetrahydrothiopyran-3-yl | 6.85 (m, 2H), 7.20 (m, 2H) |
| 18.05 | Ethyl | 2H-Tetrahydropyran-4-yl | 4.00 (m, 2H), 6.85 (m, 2H), 7.20 (m, 2H) |
| 18.06 | n-Propyl | 2H-Tetrahydropyran-4-yl | 4.00 (m, 2H), 6.85 (m, 2H), 7.20 (m, 2H) |
| 18.07 | Ethyl | 2,4,6-Trimethylphenyl | |
| 18.08 | Ethyl | 1-Methylthiocyclo-prop-1-yl | |
| 18.09 | n-Propyl | 2-(Ethylthio)prop-1-yl | |
| 18.10 | Ethyl | 2-(4-Fluorophenylthio)-ethyl | |
| 18.11 | n-Propyl | 1,3-Dimethylpyrazol-5-yl | |
| 18.12 | n-Propyl | 3-Isopropylisoxazol-5-yl | |
| 18.13 | n-Propyl | N-(Ethylsulfonyl)-N-methylaminomethyl | |

TABLE 19

Structure I with (R² = CH₃, R³ = 4-chlorophenyl)

| No. | R¹ | R⁴ | Phys. data (¹H-NMR [in ppm]) |
|---|---|---|---|
| 19.01 | Ethyl | 2H-Tetrahydropyran-3-yl | |
| 19.02 | n-Propyl | 2H-Tetrahydropyran-3-yl | |
| 19.03 | Ethyl | 2H-Tetrahydrothiopyran-3-yl | |
| 19.04 | n-Propyl | 2H-Tetrahydrothiopyran-3-yl | 0.9–1.0 (m), 1.5–1.8 (m), 1.6–1.9 (m), 2.0–2.15 (m), 2.3–2.6 (m), 7.1–7.3 (m) |
| 19.05 | Ethyl | 2H-Tetrahydropyran-4-yl | |
| 19.06 | n-Propyl | 2H-Tetrahydropyran-4-yl | |
| 19.07 | Ethyl | 2,4,6-Trimethylphenyl | |
| 19.08 | Ethyl | 1-Methylthiocycloprop-1-yl | |
| 19.09 | n-Propyl | 2-(Ethylthio)prop-1-yl | |
| 19.10 | Ethyl | 2-(4-Fluorophenylthio)ethyl | |
| 19.11 | n-Propyl | 1,3-Dimethylpyrazol-5-yl | |
| 19.12 | n-Propyl | 3-Isopropylisoxazol-5-yl | |
| 19.13 | n-Propyl | N-(Ethylsulfonyl)-N-methylaminomethyl | |

TABLE 20

Structure I with (R² = CH₃, R³ = 2,4-difluorophenyl)

| No. | R¹ | R⁴ | Phys. data (¹H-NMR [in ppm]) |
|---|---|---|---|
| 20.01 | Ethyl | 2H-Tetrahydropyran-3-yl | |
| 20.02 | n-Propyl | 2H-Tetrahydropyran-3-yl | |
| 20.03 | Ethyl | 2H-Tetrahydrothiopyran-3-yl | |
| 20.04 | n-Propyl | 2H-Tetrahydrothiopyran-3-yl | |
| 20.05 | Ethyl | 2H-Tetrahydropyran-4-yl | |
| 20.06 | n-Propyl | 2H-Tetrahydropyran-4-yl | |
| 20.07 | Ethyl | 2,4,6-Trimethylphenyl | |
| 20.08 | Ethyl | 1-Methylthiocycloprop-1-yl | |
| 20.09 | n-Propyl | 2-(Ethylthio)prop-1-yl | |
| 20.10 | Ethyl | 2-(4-Fluorophenylthio)ethyl | |
| 20.11 | n-Propyl | 1,3-Dimethylpyrazol-5-yl | |
| 20.12 | n-Propyl | 3-Isopropylisoxazol-5-yl | |
| 20.13 | n-Propyl | N-(Ethylsulfonyl)-N-methylaminomethyl | |

TABLE 21

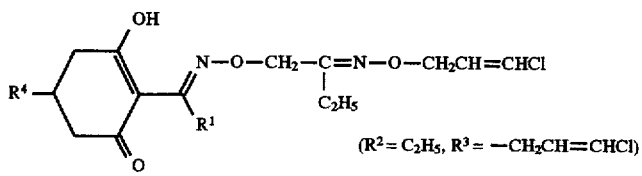

($R^2 = C_2H_5$, $R^3 = -CH_2CH=CHCl$)

I

| No. | $R^1$ | $R^4$ | Phys. data ($^1$H-NMR [in ppm]) |
|---|---|---|---|
| 21.01 | Ethyl | 2H-Tetrahydropyran-3-yl | |
| 21.02 | n-Propyl | 2H-Tetrahydropyran-3-yl | |
| 21.03 | Ethyl | 2H-Tetrahydrothiopyran-3-yl | |
| 21.04 | n-Propyl | 2H-Tetrahydrothiopyran-3-yl | 1.0–1.1 (m), 4.45–4.55 (m), 6.0–6.1 (m), 6.3–6.4 (d) |
| 21.05 | Ethyl | 2H-Tetrahydropyran-4-yl | 1.1 (m), 3.4 (m), 4.0 (m), 4.5–4.6 (m), 6.1 (m.), 6.35 (d) |
| 21.06 | n-Propyl | 2H-Tetrahydropyran-4-yl | |
| 21.07 | Ethyl | 2,4,6-Trimethylphenyl | |
| 21.08 | Ethyl | 1-Methylthiocycloprop-1-yl | |
| 21.09 | n-Propyl | 2-(Ethylthio)prop-1-yl | |
| 21.10 | Ethyl | 2-(4-Fluorophenylthio)ethyl | |
| 21.11 | n-Propyl | 1,3-Dimethylpyrazol-5-yl | |
| 21.12 | n-Propyl | 3-Isopropylisoxazol-5-yl | |
| 21.13 | n-Propyl | N-(Ethylsulfonyl)-N-methylaminomethyl | |

TABLE 22

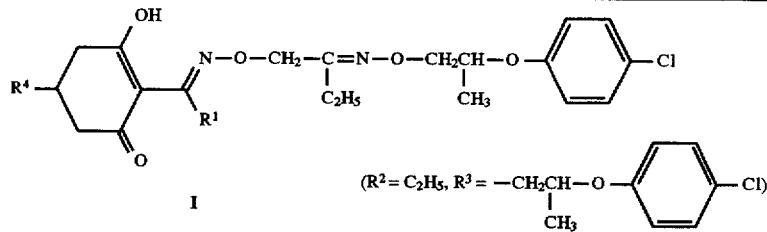

($R^2 = C_2H_5$, $R^3 = -CH_2CH(CH_3)-O-\text{(4-Cl-phenyl)}$)

I

| No. | $R^1$ | $R^4$ | Phys. data ($^1$H-NMR [in ppm]) |
|---|---|---|---|
| 22.01 | Ethyl | 2H-Tetrahydropyran-3-yl | 1.1 (m), 1.3 (m), 3.2 (m), 3.35 (m), 3.85–4.0 (m), 6.8–7.25 (m) |
| 22.02 | n-Propyl | 2H-Tetrahydropyran-3-yl | |
| 22.03 | Ethyl | 2H-Tetrahydrothiopyran-3-yl | 1.1 (m), 1.6–2.6 (m), 2.8–2.9 (m), 4.0–4.7 (m), 6.8–7.3 (m) |
| 22.04 | n-Propyl | 2H-Tetrahydrothiopyran-3-yl | 0.9–1.2 (m), 1.3–2.65 (m), 2.8–2.9 (m.), 4.2–4.7 (m), 6.7–7.2 (m) |
| 22.05 | Ethyl | 2H-Tetrahydropyran-4-yl | 1.0–1.15 (m), 1.3–1.5 (m), 1.6–1.7 (m), 1.8–1.9 (m), 2.15–2.6 (m), 2.8–2.9 (m), 3.3–3.4 (m), 3.9–4.7 (m), 6.8–7.2 (m) |
| 22.06 | n-Propyl | 2H-Tetrahydropyran-4-yl | 0.9–1.7 (m), 1.8–1.9 (m), 2.2–2.9 (m) |
| 22.07 | Ethyl | 2,4,6-Trimethylphenyl | |
| 22.08 | Ethyl | 1-Methylthiocycloprop-1-yl | |
| 22.09 | n-Propyl | 2-(Ethylthio)prop-1-yl | |
| 22.10 | Ethyl | 2-(4-Fluorophenylthio)ethyl | |
| 22.11 | n-Propyl | 1,3-Dimethylpyrazol-5-yl | |
| 22.12 | n-Propyl | 3-Isopropylisoxazol-5-yl | |
| 22.13 | n-Propyl | N-(Ethylsulfonyl)-N-methylaminomethyl | |

TABLE 23

$$\text{structure with } R^4, OH, R^1, N-O-CH_2-C(C_2H_5)=N-O-C_2H_5, O$$

I       ($R^2, R^3 = C_2H_5$)

| No. | $R^1$ | $R^4$ | Phys. data ($^1$H-NMR [in ppm]) |
|---|---|---|---|
| 23.01 | Ethyl | 2H-Tetrahydropyran-3-yl | |
| 23.02 | n-Propyl | 2H-Tetrahydropyran-3-yl | |
| 23.03 | Ethyl | 2H-Tetrahydrothiopyran-3-yl | |
| 23.04 | n-Propyl | 2H-Tetrahydrothiopyran-3-yl | 0.9–1.3 (m), 1.5–2.6 (m), 2.8–2.9 (m), 4.0–4.2 (m) |
| 23.05 | Ethyl | 2H-Tetrahydropyran-4-yl | 1.1–1.5 (m), 1.6–1.7 (m), 1.8–2.0 (m), 2.2–2.6(m), 2.8–2.9 (m), 3.3–3.4 (t), 4.0–4.2 (m) |
| 23.06 | n-Propyl | 2H-Tetrahydropyran-4-yl | |
| 23.07 | Ethyl | 2,4,6-Trimethylphenyl | |
| 23.08 | Ethyl | 1-Methylthiocycloprop-1-yl | |
| 23.09 | n-Propyl | 2-(Ethylthio)prop-1-yl | |
| 23.10 | Ethyl | 2-(4-Fluorophenylthio)ethyl | |
| 23.11 | n-Propyl | 1,3-Dimethylpyrazol-5-yl | |
| 23.12 | n-Propyl | 3-Isopropylisoxazol-5-yl | |
| 23.13 | n-Propyl | N-(Ethylsulfonyl)-N-methylaminoethyl | |

TABLE 24

*)R-configuration

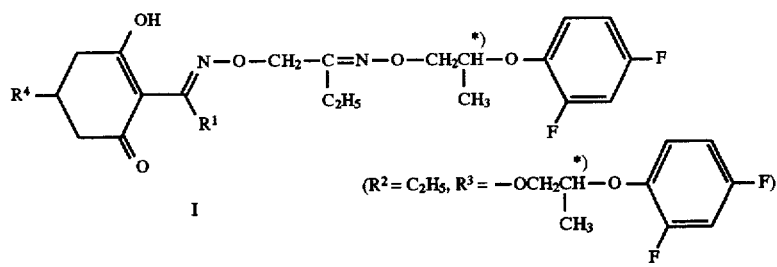

I       ($R^2 = C_2H_5$, $R^3 = -OCH_2CH(CH_3)-O-$ 2,4-difluorophenyl *))

| No. | $R^1$ | $R^4$ | Phys. data ($^1$H-NMR [in ppm]) |
|---|---|---|---|
| 24.01 | Ethyl | 2H-Tetrahydropyran-3-yl | |
| 24.02 | n-Propyl | 2H-Tetrahydropyran-3-yl | |
| 24.03 | Ethyl | 2H-Tetrahydrothiopyran-3-yl | 1.0–1.4 (m), 1.6–2.9 (m), 4.1–4.3 (m), 4.5–4.6 (m), 6.7–7.1 (m) |
| 24.04 | n-Propyl | 2H-Tetrahydrothiopyran-3-yl | 0.9–1.2 (m), 1.3–1.4 (m), 1.5–2.9 (m), 4.1–4.3 (m), 4.5–4.6.5 (m), 6.7–7.0 (m) |
| 24.05 | Ethyl | 2H-Tetrahydropyran-4-yl | 1.0–1.2 (m), 1.3–1.5 (m), 1.6–1.7 (m), 1.8–1.9 (m), 2.15–2.9 (m), 3.3–3.4 (t), 4.0–4.1 (m), 4.1–4.35 (m), 4.5–4.7 (m), 6.7–7.0 (m) |
| 24.06 | n-Propyl | 2H-Tetrahydropyran-4-yl | |
| 24.07 | Ethyl | 2,4,6-Trimethylphenyl | |
| 24.08 | Ethyl | 1-Methylthiocycloprop-1-yl | |
| 24.09 | n-Propyl | 2-(Ethylthio)prop-1-yl | |
| 24.10 | Ethyl | 2-(4-Fluorophenylthio)ethyl | |
| 24.11 | n-Propyl | 1,3-Dimethylpyrazol-5-yl | |
| 24.12 | n-Propyl | 3-Isopropylisoxazol-5-yl | |
| 24.13 | n-Propyl | N-(Ethylsulfonyl)-N-methylaminoethyl | |

Use Examples

It was possible to show the herbicidal action of the O-(oximino)ethylcyclohexenone oxime ethers of the formula I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth, and then covered with transparent plastic hoods until the plants had taken root. This covering caused uniform germination of the test plants if this was not impaired by the active compounds.

For the purpose of post-emergence treatment, the test plants are first raised, depending on growth form, to a height of growth of from 3 to 15 cm and only then treated with the active compounds suspended or emulsified in water. The test plants are either sown directly for this purpose and raised in the same containers or they are first raised separately as seed plants and transplanted into the experimental containers a few days before treatment. The application rates for the post-emergence treatment was 0.25 and 0.125 kg/ha of active substance (a.s.).

The plants were kept in a species-specific manner at 10°–25° C. or 20°–35° C. The test period extended over 2 to 4 weeks. During this time the plants were tended and their reaction to the separate treatments was assessed.

Assessment was carried out on a scale of from 0 to 100. 100 here means no emergence of the plants or complete destruction of at least the above-ground parts and 0 no damage or normal course of growth.

The plants used in the greenhouse tests were made up of the following species:

| Botanical name | Common name |
|---|---|
| Echinochloa crus-gali | barnyard grass |
| Setaria italica | foxtail millet |
| Setaria faberii | giant foxtail |
| Setaria viridis | green foxtail |
| Orysa sativa | rice |
| Triticum aestivum | winter wheat |

The result showed that undesired grasses in wheat or rice as example crops can be very well controlled using the compounds Nos. 3.05, 4.01, 4.03 and 9.04.

We claim:

1. An O-(Oximino)ethylcyclohexenone oxime ether of the formula I

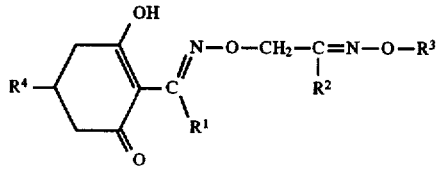

where the substituents have the following meanings:

$R^1$ is a $C_1-C_6$-alkyl group;

$R^2$ is a $C_1-C_6$-alkyl group;

$R^3$ is the phenyl group, which can be unsubstituted or can carry one to three substituents selected from the group consisting of nitro, cyano, halogen, $C_1-C_4$-alkyl and $C_1-C_4$ haloalkyl;

a $C_1-C_4$ alkyl, $C_3-C_4$ alkenyl or $C_3-C_4$ alkynyl group, these groups if desired being able to carry one of the following substituents:

halogen, $C_1-C_3$ alkyl, phenyl, which if desired, in turn can carry one to three radicals selected from the group consisting of nitro, cyano, halogen, $C_1-C_4$-alkyl, $C_1-C_4$-haloalkyl, phenyl and phenoxy, or phenoxy which, if desired, in turn can carry one to three radicals selected from the group consisting of nitro, cyano, halogen, $C_1-C_4$ alkyl and $C_1-C_4$ haloalkyl;

$R^4$ is a $C_1-C_4$-alkoxy-$C_1-C_6$-alkyl or $C_1-C_4$-alkylthio-$C_1-C_6$-alkyl group;

a phenylthio-$C_1-C_6$alkyl group, the phenyl ring if desired being able to carry one to three substituents selected from the group consisting of halogen and $C_1-C_4$-haloalkyl;

an N-($C_1-C_4$-alkylsulfonyl)-N-($C_1-C_4$-alkyl) aminomethyl group;

a $C_3-C_7$-cycloalkyl or $C_5-C_7$-cycloalkenyl group, where these groups can be unsubstituted or in each case can carry one to three substituents selected from the group consisting of hydroxyl, halogen, $C_1-C_4$-alkyl, $C_1-C_4$-alkoxy, $C_1-C_4$-alkylthio and $C_1-C_4$-haloalkyl;

a 5-membered saturated heterocycle which contains one or two oxygen and/or sulfur atoms as heteroatoms and which can be unsubstituted or can carry one to three substituents selected from the group consisting of $C_1-C_4$-alkyl, $C_1-C_4$-alkoxy, $C_1-C_4$-alkylthio and $C_1-C_4$-haloalkyl;

a 6- or 7-membered heterocycle having one or two non-adjacent oxygen and/or sulfur atoms as heteroatoms, which can be saturated or mono- or diunsaturated, where the heterocycle can be unsubstituted or can carry one to three substituents selected from the group consisting of hydroxyl, halogen, $C_1-C_4$-alkyl, $C_1-C_4$-alkoxy, $C_1-C_4$-alkylthio and $C_1-C_4$-haloalkyl;

a 5-membered heteroaromatic containing one or two nitrogen atoms and an oxygen or sulfur atom, where the heteroaromatic can be unsubstituted or can carry one to three substituents selected from the group consisting of halogen, cyano, $C_1-C_4$-alkyl, $C_1-C_4$-alkoxy, $C_1-C_4$-alkylthio, $C_1-C_4$haloalkyl, $C_2-C_6$-alkenyl, $C_2-C_6$-alkenyloxy and $C_1-C_4$-alkoxy-$C_1-C_4$-alkyl;

the phenyl or pyridyl group, where these groups can be unsubstituted or in each case can carry one to three substituents selected from the group consisting of halogen, nitro, cyano, $C_1-C_4$-alkyl, $C_1-C_4$-alkoxy, $C_1-C_4$-alkylthio, $C_1-C_4$-haloalkyl, $C_3-C_6$-alkenyloxy, $C_3-C_6$-alkynyloxy and —$NR^aR^b$, where $R^a$ is hydrogen, $C_1-C_4$-alkyl, $C_3-C_6$-alkenyl or $C_3-C_6$-alkynyl and $R^b$ is hydrogen, $C_1-C_4$-alkyl, $C_3-C_6$-alkenyl, $C_3-C_6$-alkynyl, $C_1-C_6$-acyl or benzoyl which if desired in turn can carry one to three radicals selected from the group consisting of nitro, cyano, halogen, $C_1-C_4$-alkyl, $C_1-C_4$-alkoxy, $C_1-C_4$-alkylthio and $C_1-C_4$-haloalkyl;

and the agriculturally utilizable salts of I and the esters of I with $C_1-C_{10}$-carboxylic acids or inorganic acids.

2. An O-(oximino)ethylcyclohexenone oxime ether of the formula I as defined in claim 1 where $R^3$ is a $C_1-C_4$-alkyl group bearing a phenoxy radical which is optionally substituted by one to three halogen substituents, or a $C_3$ or $C_4$-alkenyl group which is optionally substituted by a halogen substituent.

3. An O-(oximino)ethylcyclohexenone oxime ether of the formula I as defined in claim 1 where $R^4$ is a 6-membered saturated or monounsaturated heterocyle containing one oxygen or sulfur heteroatom.

4. A herbicidal composition containing a herbicidally effective amount of at least one O-(oximino) ethylcyclohexenone oxime ether of the formula I and/or of an agriculturally utilizable salt of I and/or ester of I with $C_1$–$C_{10}$-carboxylic acids or inorganic acids, as claimed in claim 1, and at least one liquid and/or solid carrier and, if desired, at least one adjuvant.

5. A process for the production of herbicidally effective compositions, which comprises mixing a herbicidally effective amount of an O-(oximino)ethylcyclohexenone oxime ether of the formula I and/or of an agriculturally utilizable salt of I and/or ester of I with $C_1$–$C_{10}$-carboxylic acids or inorganic acids, as claimed in claim 1, with at least one liquid and/or solid carrier and, if desired, with at least one adjuvant.

6. A process for controlling undesired plant growth, which comprises allowing a herbicidally effective amount of at least one O-(oximino)ethylcyclohexenone oxime ether of the formula I and/or of an agriculturally utilizable salt of I and/or ester of I with $C_1$–$C_{10}$-carboxylic acids or inorganic acids, as claimed in claim 1, to act on plants, their environment or on seeds.

* * * * *

UNITED STATES PATENT AND TRADEMARK OFFICE
CERTIFICATE OF CORRECTION

PATENT NO.: 5,739,085

DATED: April 14, 1998

INVENTOR(S): MISSLITZ et al.

It is certified that error appears in the above-identified patent and that said Letters Patent is hereby corrected as shown below:

Title page, insert the foreign application priority data as follows:

--[30]  Foreign Application Priority Data
May 5, 1994  [DE]  Germany .................. P 44 15 871.8--.

Signed and Sealed this

Twentieth Day of October, 1998

Attest:

BRUCE LEHMAN

*Attesting Officer*  *Commissioner of Patents and Trademarks*